US005728814A

United States Patent [19]

Fung et al.

[11] Patent Number: 5,728,814
[45] Date of Patent: Mar. 17, 1998

[54] GC1Q RECEPTOR, HIV-1 GP120 REGION BINDING THERETO, AND RELATED PEPTIDES AND TARGETING ANTIBODIES

[75] Inventors: Michael S. C. Fung, Houston; Bill N. C. Sun; Cecily R. Y. Sun, both of Bellaire, all of Tex.; Young Woo Kim, Plainsboro, N.J.; Liming Yu, Houston, Tex.

[73] Assignee: Tanox Biosystems, Inc., Houston, Tex.

[21] Appl. No.: 707,801

[22] Filed: Sep. 4, 1996

Related U.S. Application Data

[62] Division of Ser. No. 410,360, Mar. 24, 1995.
[51] Int. Cl.$^6$ ............................ C07K 16/00; C12D 21/08
[52] U.S. Cl. .................. 530/388.35; 530/388.7; 530/389.4; 530/389.6; 435/346; 435/339.1
[58] Field of Search ......................... 435/240.27, 346, 435/339.1; 530/300, 350, 387.1, 387.5, 388.1, 388.35, 388.7, 389.4, 389.6; 424/148.1, 153.1

[56] References Cited

PUBLICATIONS

Rudinger, J. Peptide Hormones. Parsons (Ed.), University Park Press, Baltimore, MD, pp. 1–7, Jun. 1976.
Leonard, C. K. et al. J. Biol. Chem. 265: 10373–10382, Jun. 1990.
Luo, Y. et al. J. Virol. 68: 3850–3856, Jun. 1994.
Ghebrehiwet, B. et al. J. Exp. Med. 179: 1809–1821, Jun. 1994.
Peerscke, E. I. B. et al. J. Immunol. 152: 5896–5901, Jun. 1994.

*Primary Examiner*—Christina Y. Chan
*Assistant Examiner*—Evelyn Rabin
*Attorney, Agent, or Firm*—Eric P. Mirabel

[57] ABSTRACT

Disclosed are immunogens and peptides based on the binding site of gC1q-R for HIV-1 gp120, and immunogens and peptides based on the binding site of HIV-1 gp120 for gC1q-R. The sequence of the gC1q-R binding site for gp120 is shown in SEQ D NO.: 2. The sequence of the HIV-1 gp120 binding site for gC1q-R is shown in SEQ ID NO.: 3. Also disclosed are antibodies and binding molecules to all such immunogens and peptides, and inducing the endogenous production of such antibodies.

2 Claims, 13 Drawing Sheets

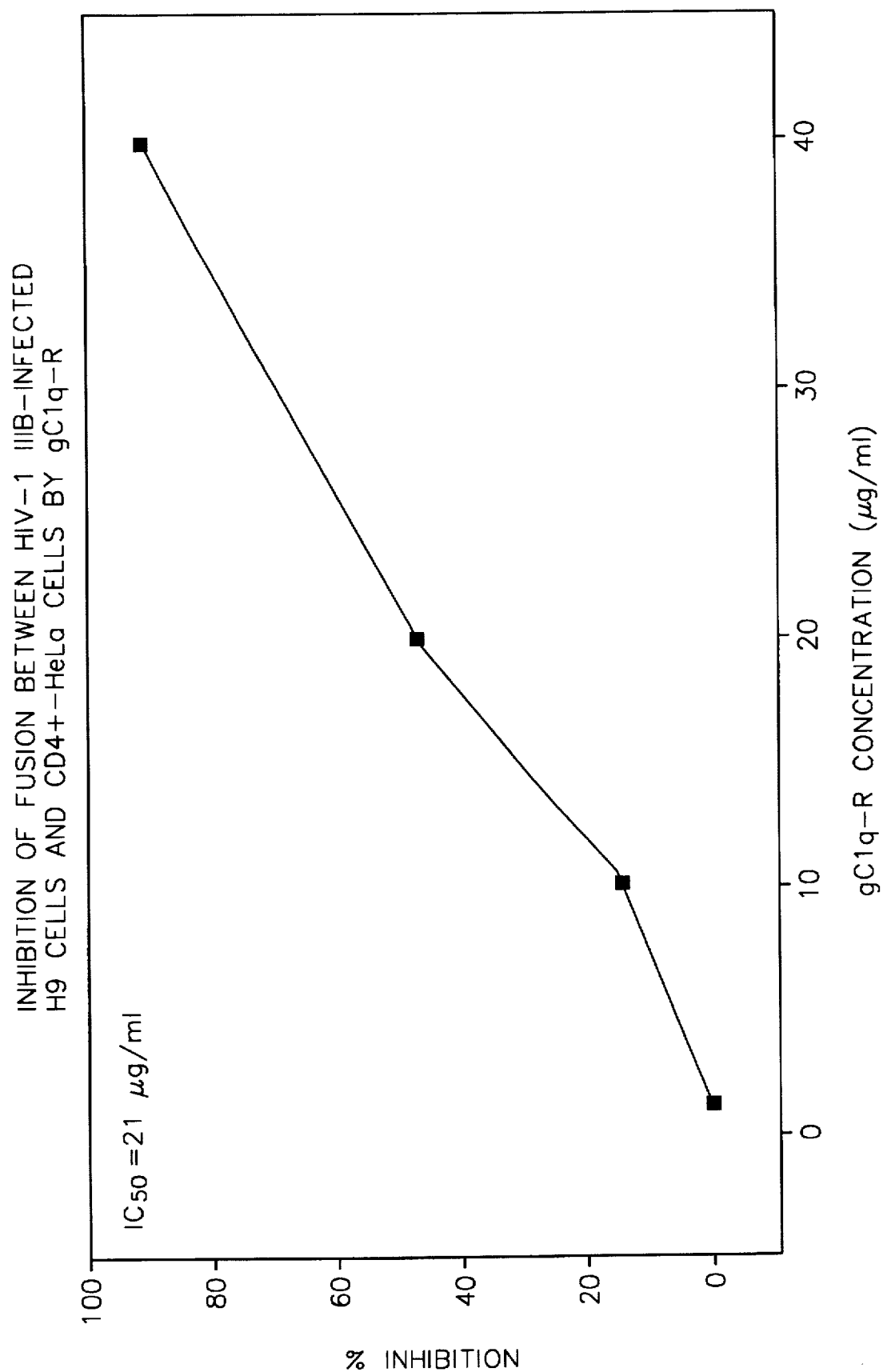

REACTIVITY OF gC1q-R WITH HIV-1 gp120 PEPTIDES RC16GG, RC12LT, AND TG12NN

FIG. 11

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1138 nucleotides
        ( B ) TYPE: nucleic acid
        ( C ) STRANDEDNESS: double stranded
        ( D ) TOPOLOGY: linear ( x i ) SEQUENCE DESCRIPTION: SEQ ID NO:1:

```
CCGGCGGCGC  CTCAGGTCGC  GGGGCGCCTA  GGCCTGGGTT     40

GTCCTTTGCA  TCTGCACGTG  TTCGCAGTCG  TTTCCGCG       78

ATG  CTG  CCT  CTG  CTG  CGC  TGC  GTG  CCC  CGT  GTG  CTG  GGC  TCC  TCC   123
Met  Leu  Pro  Leu  Leu  Arg  Cys  Val  Pro  Arg  Val  Leu  Gly  Ser  Ser
               5                        10                        15

GTC  GCC  GGC  CTC  CGC  GCT  GCC  GCG  CCC  GCC  TCG  CCT  TTC  CGG  CAG   168
Val  Ala  Gly  Leu  Arg  Ala  Ala  Ala  Pro  Ala  Ser  Pro  Phe  Arg  Gln
              20                        25                        30

CTC  CTG  CAG  CCG  GCA  CCC  CGG  CTG  TGC  ACC  CGG  CCC  TTC  GGG  CTG   213
Leu  Leu  Gln  Pro  Ala  Pro  Arg  Leu  Cys  Thr  Arg  Pro  Phe  Gly  Leu
              35                        40                        45

CTC  AGC  GTG  CGC  GCA  GGT  TCC  GAG  CGG  CGG  CCG  GGC  CTC  CTG  CGG   258
Leu  Ser  Val  Arg  Ala  Gly  Ser  Glu  Arg  Arg  Pro  Gly  Leu  Leu  Arg
              50                        55                        60

CCT  CGC  GGA  CCC  TGC  GCC  TGT  GGC  TGT  GGC  TGC  GGC  TCG  CTG  CAC   303
Pro  Arg  Gly  Pro  Cys  Ala  Cys  Gly  Cys  Gly  Cys  Gly  Ser  Leu  His
              65                        70                        75

ACC  GAC  GGA  GAC  AAA  GCT  TTT  GTT  GAT  TTC  CTG  AGT  GAT  GAA  ATT   348
Thr  Asp  Gly  Asp  Lys  Ala  Phe  Val  Asp  Phe  Leu  Ser  Asp  Glu  Ile
              80                        85                        90

AAG  GAG  GAA  AGA  AAA  ATT  CAG  AAG  CAT  AAA  ACC  CTC  CCT  AAG  ATG   393
Lys  Glu  Glu  Arg  Lys  Ile  Gln  Lys  His  Lys  Thr  Leu  Pro  Lys  Met
              95                       100                       105

TCT  GGA  GGT  TGG  GAG  CTG  GAA  CTG  AAT  GGG  ACA  GAA  GCG  AAA  TTA   438
Ser  Gly  Gly  Trp  Glu  Leu  Glu  Leu  Asn  Gly  Thr  Glu  Ala  Lys  Leu
             110                       115                       120

GTG  CGG  AAA  GTT  GCC  GGG  GAA  AAA  ATC  ACG  GTC  ACT  TTC  AAC  ATT   483
Val  Arg  Lys  Val  Ala  Gly  Glu  Lys  Ile  Thr  Val  Thr  Phe  Asn  Ile
             125                       130                       135

AAC  AAC  AGC  ATC  CCA  CCA  ACA  TTT  GAT  GGT  GAG  GAG  GAA  CCC  TCG   528
Asn  Asn  Ser  Ile  Pro  Pro  Thr  Phe  Asp  Gly  Glu  Glu  Glu  Pro  Ser
             140                       145                       150

CAA  GGG  CAG  AAG  GTT  GAA  GAA  CAG  GAG  CCT  GAA  CTG  ACA  TCA  ACT   573
Gln  Gly  Gln  Lys  Val  Glu  Glu  Gln  Glu  Pro  Glu  Leu  Thr  Ser  Thr
             155                       160                       165

CCC  AAT  TTC  GTG  GTT  GAA  GTT  ATA  AAG  AAT  GAT  GAT  GGC  AAG  AAG   618
Pro  Asn  Phe  Val  Val  Glu  Val  Ile  Lys  Asn  Asp  Asp  Gly  Lys  Lys
             170                       175                       180

GCC  CTT  GTG  TTG  GAC  TGT  CAT  TAT  CCA  GAG  GAT  GAG  GTT  GGA  CAA   663
Ala  Leu  Val  Leu  Asp  Cys  His  Tyr  Pro  Glu  Asp  Glu  Val  Gly  Gln
             185                       190                       195

GAA  GAC  GAG  GCT  GAG  AGT  GAC  ATC  TTC  TCT  ATC  AGG  GAA  GTT  AGC   708
```

```
          Glu Asp Glu Ala Glu Ser Asp Ile Phe Ser Ile Arg Glu Val Ser
                          200                 205                 210

TTT CAG TCC ACT GGC GAG TCT GAA TGG AAG GAT ACT AAT TAT ACA       753
Phe Gln Ser Thr Gly Glu Ser Glu Trp Lys Asp Thr Asn Tyr Thr
                215                 220                 225

CTC AAC ACA GAT TCC TTG GAC TGG GCC TTA TAT GAC CAC CTA ATG       798
Leu Asn Thr Asp Ser Leu Asp Trp Ala Leu Tyr Asp His Leu Met
                230                 235                 240

GAT TTC CTT GCC GAC CGA GGG GTG GAC AAC ACT TTT GCA GAT GAG       843
Asp Phe Leu Ala Asp Arg Gly Val Asp Asn Thr Phe Ala Asp Glu
                245                 250                 255

CTG GTG GAG CTC AGC ACA GCC CTG GAG CAC CAG GAG TAC ATT ACT       888
Leu Val Glu Leu Ser Thr Ala Leu Glu His Gln Glu Tyr Ile Thr
                260                 265                 270

TTT CTT GAA GAC CTC AAG AGT TTT GTC AAG AGC CAG                   924
Phe Leu Glu Asp Leu Lys Ser Phe Val Lys Ser Gln
                275                 280

TAGAGCAGAC AGATGCTGAA AGCCATAGTT TCATGGCAGG                       964

CTTTGGCCAG TGAACAAATC CTACTCTGAA GCTAGACATG                      1004

TGCTTTGAAA TGATTATCAT CCTAATATCA TGGGGAAAA                       1044

AATACCAAAT TTAAATTATA TGTTTTGTGT TCTCATTTAT                      1084

TATCATTTTT TTCTGTACAA TCTATTATTT CTAGATTTTT                      1124

GTATAACATG ATAG                                         1138
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:2:

```
Leu Met Asp Phe Leu Ala Asp Arg Gly Val Asp Asn
                5                   10
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( x i ) SEQUENCE DESCRIPTION: SEQ ID NO:3:

```
Arg Cys Ser Ser Asn Ile Thr Gly Leu Leu Thr Arg Asp Gly Gly
                5                   10                  15
```

( 2 ) INFORMATION FOR SEQ ID NO:4:

( i ) SEQUENCE CHARACTERISTICS:
        ( A ) LENGTH: 26 nucleotides
        ( B ) TYPE: nucleic acid
        ( C ) STRANDEDNESS: double stranded
        ( D ) TOPOLOGY: linear ( x i ) SEQUENCE DESCRIPTION: SEQ ID NO:4:

TACATATGCT GCACACCGAC GGAGAC       26

( 2 ) INFORMATION FOR SEQ ID NO:5:

( i ) SEQUENCE CHARACTERISTICS:
        ( A ) LENGTH: 24 nucleotides
        ( B ) TYPE: nucleic acid (C) STRANDEDNESS: double stranded
(D) TOPOLOGY: linear (x i) SEQUENCE DESCRIPTION: SEQ ID NO:5:

GCCCTGCAGC ATCTGTCTGC TCTA 24

(2) INFORMATION FOR SEQ ID NO:6:

(i) SEQUENCE CHARACTERISTICS:
(A) LENGTH: 25 nucleotides
(B) TYPE: nucleic acid
(C) STRANDEDNESS: double stranded
(D) TOPOLOGY: linear (x i) SEQUENCE DESCRIPTION: SEQ ID NO:6:

AAGAATTCCG GTCACTTTCA ACATT 25

(2) INFORMATION FOR SEQ ID NO:7:

(i) SEQUENCE CHARACTERISTICS:
(A) LENGTH: 15 amino acids
(B) TYPE: amino acid
(D) TOPOLOGY: linear (x i) SEQUENCE DESCRIPTION: SEQ ID NO:7:

Arg Ile Gln Arg Gly Pro Gly Arg Ala Phe Val Thr Ile Gly Lys
                  5                   10                  15

(2) INFORMATION FOR SEQ ID NO:8:

(i) SEQUENCE CHARACTERISTICS:
(A) LENGTH: 18 amino acids
(B) TYPE: amino acid
(D) TOPOLOGY: linear (x i) SEQUENCE DESCRIPTION: SEQ ID NO:8:

Thr Asp Gly Asp Lys Ala Phe Val Asp Phe Leu Ser Asp Glu Ile Lys Glu Glu
                  5                   10                  15

(2) INFORMATION FOR SEQ ID NO:9:

(i) SEQUENCE CHARACTERISTICS:
(A) LENGTH: 15 amino acids
(B) TYPE: amino acid
(D) TOPOLOGY: linear (x i) SEQUENCE DESCRIPTION: SEQ ID NO:9:

Ile Ile Asn Met Trp Gln Lys Val Gly Lys Ala Met Tyr Ala Pro
                  5                   10                  15

(2) INFORMATION FOR SEQ ID NO:10:

(i) SEQUENCE CHARACTERISTICS:
(A) LENGTH: 15 amino acids
(B) TYPE: amino acid
(D) TOPOLOGY: linear (x i) SEQUENCE DESCRIPTION: SEQ ID NO:10:

Ala Pro Thr Lys Ala Lys Arg Arg Val Val Gln Arg Glu Lys Arg
                  5                   10                  15

(2) INFORMATION FOR SEQ ID NO:11:

(i) SEQUENCE CHARACTERISTICS:
(A) LENGTH: 15 amino acids
(B) TYPE: amino acid
(D) TOPOLOGY: linear ( x i ) SEQUENCE DESCRIPTION: SEQ ID NO:11:

Val Gln Lys Glu Tyr Ala Phe Phe Tyr Lys Leu Asp Ile Ile Pro
            5                   10                      15

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:12:

Arg Cys Ser Ser Asn Ile Thr Gly Leu Leu Leu Thr
            5                   10

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:13:

Thr Gly Leu Leu Leu Thr Arg Asp Gly Gly Asn Asn
            5                   10

GC1Q RECEPTOR, HIV-1 GP120 REGION BINDING THERETO, AND RELATED PEPTIDES AND TARGETING ANTIBODIES

This application is a divisional of application Ser. No. 08/410,360, filed on Mar. 24, 1995 (pending).

FIELD OF THE INVENTION

The invention is related to (1) peptides which bind to HIV-1 gp120 and which are based on the gC1q receptor (gC1q-R), as well as antibodies to such peptides; (2) HIV-1 gp120 related peptides which bind to gC1q-R, and antibodies to such peptides.

BACKGROUND OF THE INVENTION

C1q is a component of the C1 complex of the classical complement pathway (R. B. Sire and K. B. M. Reid, *Immunology Today* 1991; 12:307–311). The biological functions of C1q are diverse, including initiation of the complement cascade for opsonization and cytolysis, and mediation of several different functions depending on the con types expressing the C1q receptor. C1q enhances FcR and CR1-mediated phagocytosis in monocytes/macrophages (D. A. Bobak et al., *Eur. J. Immunol.* 1988; 18:2001–2007; D. A. Bobak et al., *J. Immunol* 1987; 138:1150–1156), stimulates immunoglobulin production by B cells (K. R. Young et al., *J. Immunol.* 1991; 146:3356–3364), activates platelets to express $\alpha IIb/\beta_3$ integrins, P-selectin, and procoagulant activity (E. I. B. Peerschke et al., *J. Exp. Med.* 1993; 178:579–587; E. I. B. Peerschke et al., *J. Immunol.* 1994; 152:5896–5901), activates tumor cytotoxicity of macrophages (R. W. Leu et al., *J. Immunol.* 1990; 144:2281–2286), and exerts anti-proliferative effects on T cell growth (A. Chen et al., *J. Immunol.* 1994; 153:1430–1440).

A 33 kilodalton (kD) receptor, designated gC1q-R, which binds to the globular head of C1q molecules has been recently identified, cloned and sequenced (B. Ghebrehiwet et al., *J. Exp. Med.* 1994; 179:1809–1821; E. I. B. Peerschke et al., *J. Immunol.* 1994; 152:5896–5901; A. Chen et al., *J. Immunol.* 1994; 153:1430–1440). Another 60 kD receptor, designated cC1q-R, binds to the amino-terminal collagen-like region of C1q (B. Ghebrehiwet, Behring Inst. Mitt. 1989; 84:204–215; A. Chen et al., *J. Immunol.* 1994; 153:1430–1440). Based on the detection of gC1q-R mRNA by polymerase chain reaction (PCR) amplification and gC1q-R protein expression by immunochemical methods, this receptor was found to exist on a large number of different cell types, e.g. B cells, T cells, monocytes/macrophages, neutrophils, eosinophils, fibroblasts, platelets, endothelial cells, liver cells, neural cells and smooth muscle cells. It was not known, however, that gC1q-R binds to HIV-1 gp120 and neutralizes the infectivity of HIV-1.

It is well established that the CD4 antigen, which is expressed mainly on the surface of the helper/inducer T cells, is the primary receptor for HIV-1 gp120 (P. J. Maddon et al., *Cell* 1986; 47:333–385; J. S. McDougal et al., *Science* 1986; 231:382–385). In addition to the $CD4^+$ T cells, HIV-1 can bind to and infect a number of other cell types, such as monocytes/macrophages, B cells, colon epithelial cells and neuroglial cells, which express either undetectable or at most low levels of cell-surface CD4. Several alternative receptors have been suggested to be associated with HIV-1 infection of target cells, e.g. galactosylceramide (Gal-Cer) on the surface of human colon epithelial cells, Schwann cells, and oligodendrocytes (N. Yahl et al., *Virology* 1994; 204:550–557; J. M. Harouse et al., *Science* 1991; 253:320–323), human immunoglobulin $V_H3$ gene products of IgM isotype (mol. wt. 950 kD) on B cells (L. Berberian et al., *Science* 1993; 261:1588–1591), CD26 (mol. wt. 110 kD) on activated T and B cells (C. Callebaut et al., *Science* 1993; 262:2045–2050), and a membrane-associated C-type lectin (mol. wt. 46 kD) mainly on macrophages (B. M. Curtis et al., *Proc. Natl. Acad. Sci. USA* 1992; 89:8356–8360).

This invention was made in the course of research to find cellular binding proteins or receptors for HIV-1 gp120 on non-CD4 expressing cells. To this end, lysates of CEM-SS cells (which are T cells expressing a high level of cell-surface CD4) obtained from P. J. Nara (*AIDS Res. Hum. Retroviruses* 1987; 3:283–302) and DAKIKI cells (which are CD4-negative B cells) obtained from American Type Culture Collection (Rockville, Md.) were run on sodium dodecyl sulfate-polyacrylamide gel electrophoresis (SDS-PAGE), and the separated proteins were transblotted onto nitrocellulose membranes for Western immunoblot assays. It was found that recombinant or HIV-1-infected cell derived gp120 reacted with a protein band of 32–33 kD in Both CEM-SS and DAKIKI cell lysates, which was distinct from the 55 kD protein band reactive with anti-human CD4 monoclonal antibodies.

In order to purify this novel gp120-binding protein for identification By N-terminal amino acid sequencing, a large quantity of DAKIKI cell lysate was prepared. The gp120-binding protein was partially purified by preparative electrophoresis using Prep Cell Model 491 (Bio-Rad Laboratories, Inc., Hercules, Calif.). The sample was then run on 2-dimensional gel electrophoresis and blotted onto polyvinylidene difluoride (PVDF) membrane for Western immunoblotting to identify the gp120-reacting protein spot and for N-terminal amino acid sequencing. It was determined that the sequence of the first fifteen amino acids at the N-terminus of the gp120-reacting protein was identical to that of the protein previously identified as p32 (mol. wt. 32 kD), which was co-purified with a human pre-mRNA splicing factor by A. R. Krainer et al. (*Cell* 1991; 66:383–394) and B. Honoré et al. (*Gene* 1993; 134:282–287). Further experiments revealed that DAKIKI cells can be stained by rabbit anti-p32 immunoglobulins which were generated by using purified *E. coli* expressed p32 as the immunogen, showing that p32 exists on the cell surface of DAKIKI cells. DAKIKI cells were also shown to bind recombinant HIV-1 gp120, even though the cells do not express detectable CD4 on the cell surface by immunofluorescence methods. Taken together, these findings show that p32 is an alternative cell-surface binding protein for HIV-1 gp120. Subsequently, it was determined that p32 has the same sequence as gC1q-R (SEQ ID NO.: 1) (B. B. Ghebrehiwet et al., *J. Exp. Med.* 1994; 179:1809–1821).

The precursor or pre-proprotein of gC1q-R has 282 ammo acids (a.a.), and the functional mature protein has 209 a.a. This mature protein contains the peptidic portion between amino acid residue nos.: 74 (leucine) and 282 (glutamine), of SEQ ID NO.: 1. Mature gC1q-R protein is highly charged and acidic. It has three potential N-glycosylation sites at amino acid positions: 114, 135 and 223. As a result, the apparent molecular weight of gC1q-R in SDS-PAGE is 32 kD, instead of 24.3 kD as calculated from the amino acid composition. Since the mature protein has only one cysteine residue at position 186, there is no intrachain disulfide linkage within the protein. gC1q-R is found in a wide variety of cell types, such as B cells, T cells, monocytes/macrophages, esosinophils, neutrophils, platelets, endothelial cells, fibroblasts, and liver cells.

Inasmuch as gC1q-R is associated with multiple immunological and physiological functions, the interaction between gC1q-R and HIV-1 gp120 may account for some of the immunological and physiological dysfunctions manifested by HIV-1-infected individuals. It may also result in the known ability of HIV-1 to infect a wide variety of non-CD4 expressing human cells in different tissues and organs. Intervention in the interaction between gC1q-R and HIV-1 gp120 represents a new strategy in combating HIV-1 disease. Several inventions based on this intervention strategy are discussed below.

SUMMARY OF THE INVENTION

The invention includes immunogens and peptides based on the binding site of gC1q-R for HIV-1 gp120, and immunogens and peptides based on the binding site of HIV-1 gp120 for gC1q-R. The sequence of the gC1q-R binding site for gp120 is shown in SEQ ID NO.: 2. The sequence of the HIV-1 gp120 binding site for gC1q-R is shown in SEQ ID NO.: 3. The invention also includes antibodies and binding molecules to all such immunogens and peptides, and inducing the endogenous production of such antibodies. Other aspects and embodiments of the invention are described further below. The hybridoma cell line producing the antibody 99-12-1 was deposited at the American Type Culture Collection, 12301 Parklawn Drive, Rockville, Md., 20852, on Mar. 23, 1995, and assigned deposit designation HB 11863.

BRIEF DESCRIPTION OF THE DRAWINGS

FIG. 4 shows the inhibition of fusion between HIV-1IIIB-infected H9 cells and CD4+-HeLa cells by gC1q-R.

FIG. 11 shows the reactivity of gC1q-R with the HIV-1 gp120 C4 region peptides RC12LT, TG12NN, and RC16GG. The line marked with solid triangles represents RC16GG, the line marked with solid circles represents TG12NN, and the line marked with solid squares represents RC12LT. The Y axis represents the reactivity of gC1q-R with the peptides expressed as OD at 450 nm and the X axis is the concentration of gC1q-R in solution.

Making and Using the Invention

A. gC1q-R Peptides

Figure 1:
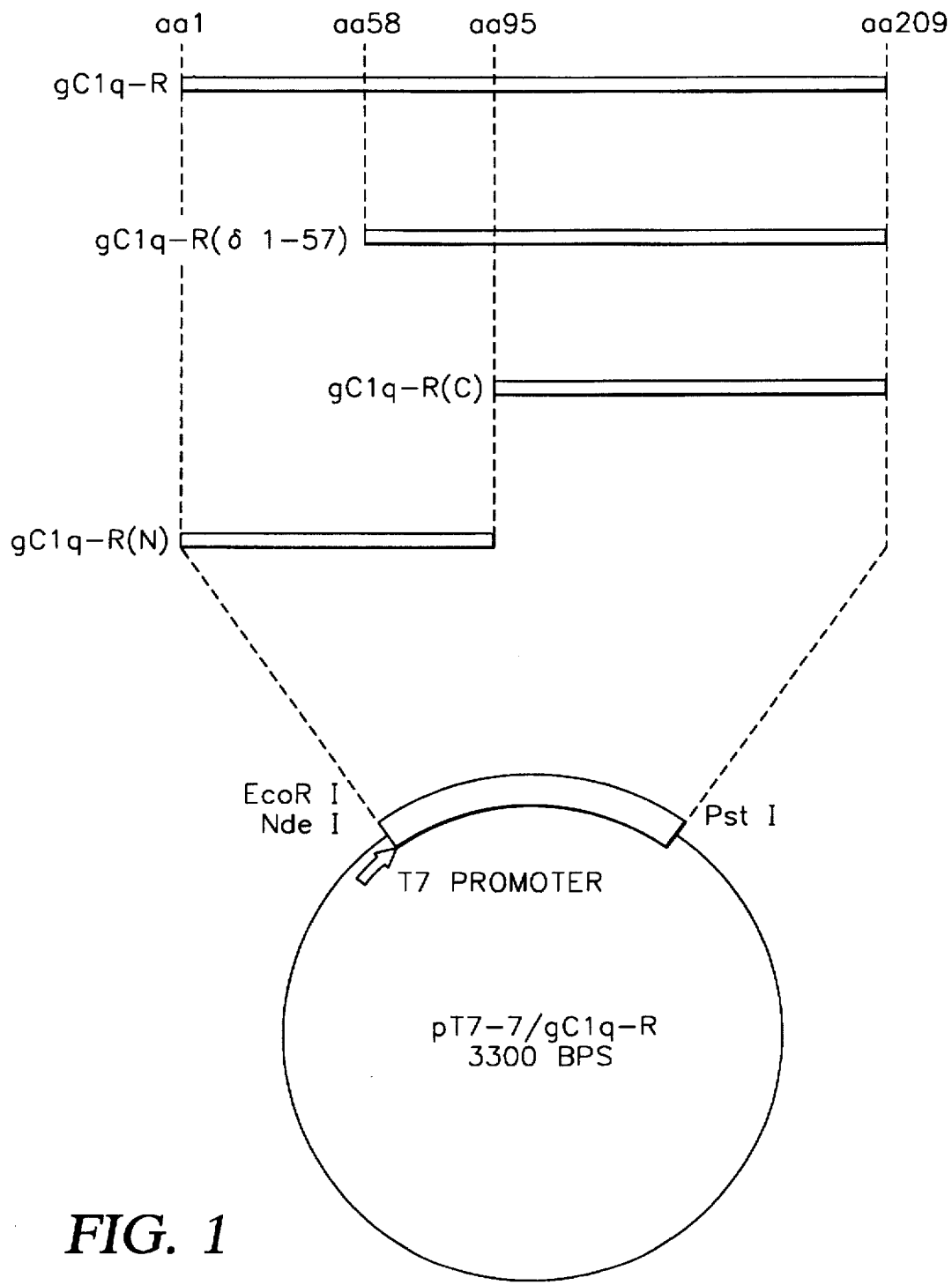
FIG. 1 is a restriction map of the vector pT7-7 used to express in *E. coli* the full-length mature form of gC1q-R (1–209 a.a.) and its three truncated forms. gC1q-R (δ1–57) represents gC1q-R (58–209 a.a.), gC1q-R(C) represents gC1q-R (95–209 a.a.), and gC1q-R(N) represents (1–94 a.a.).

The complete nucleotide and deduced amino acid sequences of gC1q-R are shown in SEQ ID NO.: 1. The recombinant gC1q-R which was expressed in *E. coli* and used in the immunizations and other examples described below is the entire C-terminal segment starting from the leucine at amino acid residue number 74 in SEQ ID NO.: 1. This segment represents the soluble, mature protein of gC1q-R which was characterized. The N-terminal segment may represent a hydrophobic membrane anchor in the pre-proprotein.

The peptidic segment encompassing amino acid residue numbers 239 to 250 of SEQ ID NO.: 1 was identified as the active binding site for gp120, based on the complete inhibition of gp120 binding to gC1q-R by an anti-gC1q-R monoclonal antibody 99-12-1 (which binds to the peptide of SEQ ID NO.: 2) as discussed below under Example 10.

The active binding site of gC1q-R for gp120 can be expressed as a distinct peptide (hereinafter "the gp120 binding site"), or any longer peptide which includes the gp120 binding site (such as, for example, the peptide representing the entire gC1q-R sequence) (see Example 1 below), or the gp120 binding site or such longer peptides can be linked to another protein such as keyhole limpet hemocyanin (KLH) or another carrier molecule which enhances its immunogenicity, or the gp120 binding site can be bound to a peptide or molecule engendering an immunogenic configuration to enhance its immunogenicity, or a peptide which is structurally or immunologically equivalent to the gp120 binding site can be used for the same purpose (all such peptides hereinafter referred to as the "gp120 Binding Site Peptides").

The gp120 Binding Site Peptides are useful for detecting or quantitating HIV-1 gp120, HIV-1 virions or HIV-1-infected cells in a diagnostic assay. Such a diagnostic assay can use a standard assay format, such as an enzyme-linked immunosorbent assay (ELISA). In an ELISA, the gp120 Binding Site Peptides can be immobilized on inert solid matrices or magnetic beads, either directly or indirectly through a cross-linking agent or a specific binding agent. The biological fluid test samples are then incubated with the coated matrices. Free HIV-1 gp120 molecules or HIV-1 virions bearing gp120 molecules reactive with the gp120 Binding Site Peptides will bind to the matrices. The bound HIV-1 gp120 molecules or HIV-1 virions can then be detected with either monoclonal or polyclonal anti-HIV-1 antibodies, which can then be reacted with enzyme-linked secondary detecting antibodies for quantitation based on color reaction. Alternatively, the captured gp120 or virions can be detected by other means, e.g. fluorescence, chemilumminescence, radioactivity counting, or PCR.

The gp120 Binding Site Peptides can also be used to detect and quantitate HIV-1-infected cells in patient's blood samples or other specimens by either direct or indirect immunochemical procedures. For example, in one such assay, the infected cells are contacted with the gp120 Binding Site Peptides and then labeled with antibodies binding thereto. These detecting antibodies can be directly or indirectly conjugated with a fluorescent probe. Immunofluorescence is then detected by viewing the cells under a fluorescence microscope, or by flow cytometric methods. Alternatively the gp120 Binding Site Peptides can be labeled directly with enzymes, radionuclides, fluorescent probes or biotin. The labeled peptides bound to the cells can then be detected correspondingly by well established methods.

The gp120 Binding Site Peptides, or any derivative products such as conjugates with a toxin (e.g. ricin A, diphtheria toxin, *Pseudomonas aeruginosa* exotoxin A, pokeweed antiviral protein), a high-energy radionuclide (e.g. iodine-131, indium-111, and yttrium-90), a cytotoxic drug (e.g. doxorubicin), a cell membrane-active molecule (e.g. phospholipase, complements, and saponin), or as a microcarrier (such as liposomes) can also be used in treatment of HIV-1 disease or prevention of HIV-1 infection. The peptide corresponding to the entire sequence of the mature protein of gC1q-R has been shown to neutralize the in vitro infectivity of several divergent strains of HIV-1 and to inhibit syncytium formation between CD4-positive cells and cells infected with HIV-1IIIB. See Examples 5 and 6 below. Administration of the gp120 Binding Site Peptides would also be expected to bind to gp120 and neutralize HIV-1, and also to prevent HIV-1 from infecting other cells through cell-to-cell fusion (syncytium formation). Such administration could serve as a treatment for HIV-1 disease or it could be administered prophylactically, either before or immediately after exposure to HIV-1, to prevent or inhibit HIV-1 infection. In prophylactic use, it could be administered to high-risk groups, such as intravenous drug users and health care workers, as a preventive measure. Alternatively, it could be used following a needle-stick injury to prevent infection, or just before or immediately after birth to prevent mother-to-baby HIV-1 transmission.

The gp120 Binding Site Peptides can be conjugated to solid matrices. These modified matrices can be used extracorporeally to remove free HIV-1 virions or HIV-1 infected cells from HIV-1-infected individuals in order to reduce viral loads.

B. Antibodies to gC1q-R Peptides

Monoclonal or polyclonal antibodies against gC1q-R can be readily made with well known techniques as described below in Example 2. Such monoclonal antibodies could be generated using monovalent or polyvalent gC1q-R, or the gp120 Binding Site Peptides, as immunogens. The gC1q-R peptide (or the gp120 Binding Site Peptides) can also be used to screen for the hybridomas following immunization and fusion. Another alternative is to make immunogens using any of the gp120 Binding Site Peptides or equivalent peptides having the ability to bind to the relevant part of the gp120 C4 region in combination with one or more protein carriers. Preferred protein carriers are KLH, tetanus toxoid or Bacillus Calmette-Guerin (BCG). Recombinant protein antigens such as those from vaccinia virus, hepatitis B virus, adenovirus, or influenza virus can also be used. These carriers can be chemically conjugated to the g-p120 Binding Site Peptides, or the entire carrier-peptide can be expressed by a recombinant host cell. Polyclonal antibodies can be generated in animals (e.g. rodents, sheep, goats, guinea pigs, rabbits, and non-human primates) using the gp120 Binding Site Peptides or equivalent peptides as immunogens (see Example 3 below).

Monoclonal or polyclonal antibodies specific to the gp120 binding site of gC1q-R can also be generated by immunizing animals with deoxyoligonucleotides encoding the gp120 Binding Site Peptides as DNA immunogens (J. J. Donnelly et al., *J. Immunol. Meth.* 1994; 176:145–152). The specific oligonucleotides encoding gC1q-R can be constructed together with other expression vectors (e.g. vaccinia virus, hepatitis B virus, cytomegalovirus, retroviruses, or adenoviruses) for enhancing expression and gene targeting. Alternatively direct intramuscular injection, mechanical procedures such as high-velocity gold microprojectiles coated with DNA to transfect epidermis, or ex-vivo transfections by chemical (e.g. calcium phosphate) or electrical means, can be employed to insert the oligonucleotides into host cells for expression of antigens to induce specific antibody response.

Such monoclonal or polyclonal antibodies have a number of uses. They can be used to detect cells which express the gC1q-R receptor, such as B cells, T cells, monocytes/macrophages, neutrophils, eosinophils, fibroblasts, platelets, and endothelial and smooth muscle cells, using an immunofluorescence assay format or others, as described above. The monoclonal antibody 99-12-1 reactive with gC1q-R has been shown to compete with gp120 for binding to gC1q-R (see experiments described under Example 11 below). Thus, they could also be used as a treatment for HIV-1 disease or, if administered prophylactically, either before or immediately after exposure to HIV-1 to prevent or inhibit HIV-1 infection.

If used in treating HIV-1 disease or to prevent infection in humans, they would preferably be used either in the form of chimeric, humanized or human antibodies. Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs) which are responsible for antigen binding and specificity are animal derived and have an amino acid sequence corresponding to the animal antibody, and substantially all of the remaining portions of the molecule are human derived and correspond in amino acid sequence to a human antibody. See L. Riechmann et al., *Nature* 1988; 332:323–327; G. Winter, U.S. Pat. No. 5,225,539; C. Queen et al., International Patent No. WO 90/07861.

Human antibodies can be made by several different ways, including by use of human immunoglobulin expression libraries (Stratagene Corp., La Jolla, Calif.) to produce fragments of human antibodies ($V_H$, $V_L$, $F_v$, Fd, Fab, or $F(ab')_2$), and using these fragments to construct whole human antibodies using techniques similar to those for producing chimeric antibodies. Human antibodies can also be produced in transgenic mice with a human immunoglobulin genome, which are produced by GenPharm International (Mountain View, Calif.). The animals are immunized with the gp120 Binding Site Peptides. Human antibodies against the gp120 Binding Site Peptides can be found in vaccinees receiving the immunogens. Hybridomas or EBV-transformed B cell lines can be developed from the B cells of the donors. Human antibodies can also be generated by combinatorial library methodology (T. A. Collet et al., *Proc. Natl. Acad. Sci. USA* 1992; 89:10026–10030), using mRNA coding for the heavy and light chains of the anti-gp120 binding site antibodies. These mRNAs can be obtained from the B cells of the vaccinees as described above.

Alternatively, one can create single peptide chain binding molecules in which the heavy and light chain $F_v$ regions are connected (J. S. Huston et al., *Proc. Natl. Acad. Sci. USA* 1983; 85:5879–5883). All of the wholly and partially human antibodies are less immunogenic than wholly murine monoclonal antibodies, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary.

Antibodies to the gp120 Binding Site Peptides can be injected into animals (e.g. mice) to raise anti-idiotypic monoclonal antibodies. The anti-idiotypes may mimic the original antigen and thus can be used as immunogens to generate antibodies against the gp120 binding site, or as gC1q-R to block HIV-1 infection.

C. HIV-1 gp120 Peptides Binding to gC1q-R

A recombinant peptide having the sequence of amino acid residue nos. 444 to 459 of HIV-1 gp120 of HXB2R strain, as shown in SEQ ID NO.: 3, was determined to bind to gC1q-R by the method described below under Example 13. This peptidic segment is located in the gp120 region designated C4 (C. K. Leonard et al., *J. Biol. Chem.* 1990; 265:10373–10382). This peptide is referred to hereinafter as "the gC1q-R Binding Site Peptide". Such a peptide, or longer peptides containing this peptide or equivalent peptides with the ability to bind to gC1q-R, could be used as immunogens to generate monoclonal or polyclonal antibodies which target such gp120 region.

A recombinant peptide having the sequence as shown in SEQ ID NO.: 3, or longer peptides including such peptides or equivalent peptides with the ability to bind to gC1q-R, or other immunogens based on such peptides (for example, made by conjugating these peptides to preferred carrier proteins such as to KLH, tetanus toxoid or BCG, or including them as a part of an immunogenic structure such as a defective or attenuated forms of hepatitis B virus, adenovirus, or influenza virus) could be used as vaccines against HIV-1 as described above. These carriers can be chemically conjugated to the gp120 Binding Site Peptides, or the entire carrier-peptide can be expressed from a recombinant host cell. When used as vaccines, they would generate antibodies endogenously, and the generated antibodies would bind to the gC1q-R binding site of gp120 and neutralize HIV-1, or they will bind to HIV-1-infected cells to inhibit viral transmission via cell-to-cell fusion or to kill infected cells by antibody dependent cellular cytotoxicity (ADCC) or complement mediated cytolysis (CMC).

Monoclonal or polyclonal antibodies specific to the binding site of gp120 for gC1q-R can also be generated by immunizing animals with deoxyoligonucleotides encoding the gC1q-R Binding Site Peptide as DNA immunogens (J. J. Donnelly et al., *J. Immunol. Meth.* 1994; 176:145–152). The specific oligonucleotides encoding this portion of gp120 can be constructed together with other expression vectors (e.g. vaccinia virus, hepatitis B virus, cytomegalovirus, retroviruses, or adenoviruses) for enhancing expression and gene targeting. Alternatively direct intramuscular injection, mechanical procedures such as high-velocity gold microprojectiles coated with DNA to transfect epidermis, or ex-vivo transfections by chemical (e.g. calcium phosphate) or electrical means, can be employed to insert the oligonucleotides into host cells for expression of antigens to induce specific antibody response.

D. Antibodies to HIV-1 gp120 Peptides

Monoclonal antibodies against SEQ ID NO.: 3, representing the gC1q-R Binding Site Peptide could be generated with conventional techniques by immunizing animals (such as rodents and non-human primates) with gp120 or such peptides, or the above-described immunogens. Polyclonal antibodies can also be generated using well known techniques, as described above.

Monoclonal or polyclonal antibodies to the gC1q-R Binding Site Peptide (in the C4 region of gp120) can also be generated in animals or humans with oligonucleotides encoding this region, or a longer region, as a DNA immunogen or vaccine as described above.

These monoclonal or polyclonal antibodies can be used for detecting or quantifying HIV-1 gp120, HIV-1 virions or HIV-1-infected cells in a diagnostic assay. Such a diagnostic assay can use a standard assay format, such as an ELISA. The ELISA is constructed in a similar manner to that described above for the gp120 Binding Site Peptides except that the anti-HIV-1 gp120 antibodies—rather than these peptides—are immobilized on inert solid matrices or magnetic beads. The biological fluid test samples are then incubated with the coated matrices. HIV-1 gp120 or HIV-1 virions bearing gp120 molecules reactive with the antibodies will bind to the matrices. The bound virions or gp120 can then be detected with other monoclonal or polyclonal anti-HIV-1 antibodies, which can then be reacted with enzyme-linked secondary detecting antibodies for quantitation based on color reaction. Alternatively, the captured gp120 or HIV-1 virions can be detected by other means, e.g. fluorescence, chemiluminescence, or PCR.

These antibodies can also be used to detect and to quantitate the HIV-1-infected cells in patient blood samples by direct or indirect immunofluorescence procedures, as described above for the gp120 Binding Site Peptides. The antibodies can also be labeled directly with enzymes, radionuclides, fluorescent probes or biotin. The labeled antibodies bound to the cells can then be detected by established methods.

Antibodies against this gC1q-R binding site in the C4 region of HIV-1 gp120 region could also potentially be used in treatment of HIV-1 disease or prevention of HIV-1 infection. They can be used individually or in combination with other anti-HIV-1 neutralizing antibodies, recombinant soluble CD4, anti-retroviral drugs or cytokines. Such antibodies would be expected to be neutralizing because once bound to gp120, they should inhibit it from binding to gC1q-R and thus preventing the subsequent infection of target cells. These antibodies would probably be in chimeric, humanized or human form when used for therapy or prevention of HIV-1 infection. The methods of generation of these forms of antibodies are described above. In addition, transgenic mice with a human immunoglobulin genome can be immunized with the gC1q-R Binding Site Peptides in order to produce human antibodies. Alternatively, human antibodies against the C4 region of gp120 can be found in HIV-1-infected individuals or vaccinees receiving the gC1q-R Binding Site Peptides containing immunogens. Hybridomas or EBV-transformed B cell lines can be developed from the B cells of these donors. Human antibodies can also be generated by the combinatorial library methodology (T. A. Collet et al., Proc. Natl. Acad. Sci. USA 1992; 89:10026–10030), using mRNA coding for the heavy and light chains of the anti-C4 antibodies. These mRNAs can be obtained from the B cells of HIV-1-infected individuals or the vaccinees as described above.

The monoclonal or polyclonal antibodies can be used to target cytotoxic agents to trill infected cells, either in the form of conjugates or microcarriers (such as liposomes). The conjugated agents can be, for example, toxins, cytotoxic drugs, membrane-active enzymes or chemicals, and high-energy radionuclides.

The antibodies to the gC1q-R binding site on gp120 can be conjugated to solid matrices. These modified matrices can be used extracorporeally to remove free HIV-1 virions or HIV-1-infected cells from HIV-1-infected individuals in order to reduce viral loads.

The antibodies to the gC1q-R Binding Site on gp120 can be modified by combining with another antibody with different specificity (e.g. to cell surface markers or HIV-1 antigens). Such bi-specific antibodies can be generating by either chemical conjugation (S. A. Kosteiny et al., J. Immunol. 1992; 148:1547–1553; A. Mabondzo et al., J. Inf. Dis. 1992; 166:93–99) or fusion of the two hybridomas (S. M. Chamow et al., J. Immunol. 1994; 153:4268–4280).

Antibodies to the gC1q-R Binding Site Peptides can be injected into animals (e.g. mice) to raise anti-idiotypic monoclonal antibodies. Anti-idiotypic monoclonal antibodies may mimic the original antigen used for generating the antibody targeted, and thus can be used as immunogens to generate antibodies against the gC1q-R Binding Site.

Exemplification of how to make and use the invention, and verification of its utility, appears below.

EXAMPLE 1

Expression of the gC1q-R Proteins in *E. coli*

A. RNA isolation and cDNA preparation: Total RNA was isolated from 5×10⁶ DAKIKI cells by the RNA-ZOL extraction method following the manufacturer's procedure (Biotecx, Houston, Tex.). Ten micrograms of the RNA were used as a template for preparing the first strand of cDNA in a reverse transcription reaction mixture which contained 50 mM Tris-HCl (pH 8.3) and 20 units of RNASIN (Promega, Madison, Wis.), 0.5 mM each of dATP, dTTP, dCTP and dGTP, 10 μM oligo dT, and 2 units of AMV reverse transcriptase (Gibco BRL, Gaithersburg, Md.). The reaction was performed at 42° C. for 1 hour.

B. PCR to amplify the gC1q-R cDNA encoding the mature full-length gC1q-R protein (from leucine at position 74 to glutamine at position 282 of SEQ ID NO.: 1). The sequences of the two primers used in the PCR were derived from the gC1q-R cDNA gene (A. R. Krainer et al., Cell 1991; 66:383–394) with the Primer No. 1 having a Nde I and Primer No. 2 a Psi I restriction sites added. (primer No. 1 SEQ ID NO.: 4 TACATATGCTGCACACCGACGGAGAC; Primer No. 2 SEQ ID NO.: 5 GCCCTGCAGCATCTGTCTGCTCTA). The PCR reaction was carried out in 50 mM KCl, 10 mM Tris-HCl (pH 8.3), 1.5 mM MgCl₂, 0.01% gelatin, 0.2 mM each of dATP, dTTP, dCTP and dGTP, 0.5 mM of each of the primers, 2 μl of the reverse transcription reaction mixture, and 1 unit of Taq DNA polymerase (United States Biochemicals, Cleveland, Ohio). PCR was conducted at 94° C. (1 minute), 55° C. (2 minutes) and 72° C. (2 minutes) for 40 cycles on the GeneAmp 9600 (Perkin Elmer, Norwalk, Conn.).

C. Construction of the gC1q-R expression vector and expression of the full-length mature recombinant protein in *E. coli*. The gC1q-R cDNA segment was cloned into the pT7-7 vector (United States Biochemicals) by double restriction enzyme Nde I and Pst I digestion (FIG. 1). The host *E. coli* strain was BL21. The cloned gene was under the control of the strong T7 promoter and was expressed upon induction by 1 mM IPTG.

D. Expression of truncated gC1q-R recombinant proteins.

A recombinant gC1q-R with its N-terminal portion truncated, designated gC1q-R(C), was produced as shown in FIG. 1. The gene segment encoding the N-terminal portion was removed from the pT7-7/gC1q-R expression vector by EcoR I and BstX I restriction digestion. gC1-R(C) contains the peptidic segment between phenylalanine at position 168 and glutamine at position 282 of SEQ ID. NO.: 1. The ends of the vector were blunted by T4 DNA polymerase and re-ligated by T4 DNA ligase. The peptide gC1q-R(C) was expressed in BL21 cells in the same way as for the full-length gC1q-R.

A recombinant gC1q-R with its C-terminal portion truncated, designated gC1q-R(N), was produced as shown in FIG. 1. gC1q-RC(N) contains the peptidic segment between leucine at position 74 and asparagine at position 167 of SEQ ID NO 1. The gene segment encoding the C-terminal portion was removed from the pT7-7/gC1q-R expression vector by BstX I and Pst I digestion. The ends of the vector were blunted by T4 DNA polymerase and re-ligated by T4 DNA ligase. The peptide gC1q-R(N) was expressed in BL21 cells in the same way as for the full-length gC1q-R.

A recombinant gC1q-R with its N-terminal 57 amino acids truncated, designated gC1q-R(δ1–57) was produced as shown in FIG. 1. gC1q-R (δ1–57) contains a peptidic segment between valine at position 131 and glutamine at position 282 of SEQ ID NO.: 1. The gene segment was first synthesized by PCR. The full-length gC1q-R cDNA, the template, and two primers, Primer No. 2, SEQ ID NO.: 5, and Primer No. 3 (SEQ ID NO.: 6), having the sequence AAGAATTCCGGTCACTTTCAACATT, were used in the PCR. The reaction conditions for the PCR is the same as above except that the amplification cycles was reduced to 25. The PCR amplified DNA segment was cloned into the pT7-7 vector by sites EcoRI and Pst I. The peptide gC1q-R(δ1–57) was expressed in BL21 cells in the same way as the full-length gC1q-R.

E. Production and purification of gC1q-R from *E. coli*

*E. coli* expressing gC1q-R was cultured and harvested by sonification in Tris buffer. The lysate was centrifuged and the supernatant dialyzed against a buffer containing 20 mM HEPES, 0.1M KCl, 0.5% glycerol, 0.2 mM EDTA and 1 mM dithiothreitol at pH 8.0. The dialyzed sample was loaded on a pre-equilibrated Fast Q ion-exchange column (Pharmacia Biotechnology, Piscataway, N.J.). The bound proteins were eluted with a buffer containing 20 mM HEPES and 1M KCl at pH 8.0. Fractions tested positive for gC1q-R by SDS-PAGE and Western immunoblot for reactivity with recombinant gp120 were collected. The pooled fractions were further purified on a Sephracryl 200 gel filtration column (Pharmacia Biotechnology). The purity of the final material was determined by SDS-PAGE and its binding activity with gp120 by ELISA (see Example 4 below).

EXAMPLE 2

Making Monoclonal Antibodies Against the gC1q-R Peptide

Male BALB/cJ mice (Jackson Laboratories, Bar Harbor, Me.) of 12 weeks old, were injected subcutaneously with 100 μg of purified E. coli expressed gC1q-R in complete Freund's adjuvant (Difco Laboratories, Detroit, Mich.) in 200 μl of PBS. One month later, the mice were injected subcutaneously with 100 μg of gC1q-R in incomplete Freund's adjuvant. Then one month later and three days prior to sacrifice, the mice were again injected subcutaneously with 100 μg of the same antigen in incomplete Freund's adjuvant. For each fusion, single cell suspensions were prepared from the spleen of an immunized mouse and used for fusion with Sp2/0 myeloma cells. $5 \times 10^8$ of the Sp2/0 cells and $5 \times 10^8$ spleen cells were fused in a medium containing 50% polyethylene glycol (M. W. 1450) (Kodak, Rochester, N.Y.) and 5% dimethylsulfoxide (Sigma Chemical Co., St. Louis, Mo.). The cells were then adjusted to $1.5 \times 10^5$ of the spleen cells per 200 μl of the suspension in Iscove medium (Gibco, Grand Island, N.Y.), supplemented with 10% fetal bovine serum, 100 units/ml of penicillin, 100 μg/ml of streptomycin, 0.1 mM hypoxanthine, 0.4 μM aminopterin, and 16 μM thymidine. Two hundred microliters of the cell suspension were added to each well of about twenty 96-well microculture plates. After about ten days culture supernatants were withdrawn for screening by ELISA with Immulon 1 microtest plates (Dynatech Laboratories, Alexandria, Va.) pre-coated with $50 \times 10^3$ DAKIKI cells per well. DAKIKI cells were tested to express gC1q-R abundantly on the surface. Briefly, wells of the microtest plates coated with dried DAKIKI cells were added with 200 μl of 5% BLOTTO (non-fat dry milk) in phosphate-buffered saline (PBS) to block the non-specific sites. An hour later, the wells were then washed with the buffer PBST (PBS containing 0.05% Tween 20). Fifty microliters of culture supernatant from each fusion web were collected and mixed with 50 μl of BLOTTO and then added to the individual webs of the microtest plates. After one hour of incubation, the wells were washed with PBST. The murine antibodies bound to the cells were then detected by reaction with horseradish peroxidase (HRP) conjugated goat anti-mouse IgG (Jackson ImmunoResearch Laboratories, West Grove, Pa.), diluted at 1:1,000 in BLOTTO. Peroxidase substrate solution containing 0.1% 3', 3', 5', 5' tetramethyl benzidine (Sigma) and 0.0003% hydrogen peroxide was added to the wells for color development. The reaction was terminated by addition of 50 μl of 2M $H_2SO_4$ per well. The optical density (OD) at 450 nm of the reaction mixture was read with a BioTek ELISA reader (BioTek Instruments, Winooski, Vt.).

The culture supernatants in those positive wells were also tested for reactivity with recombinant gC1q-R in ELISA. Briefly, to wells of Immulon 2 (Dynatech Laboratories) microtest plates 50 μl of E. coli expressed gC1q-R at 1 μg/ml was added overnight at room temperature. After the coating solution was removed by flicking of the plate, 200 μl of BLOTTO were added to each well for one hour to block the non-specific sites. The wells were then washed with PBST. The bound murine antibodies were detected as described above. The cells in those positive wells were cloned by limiting dilution. The clones were tested again for reactivity with gC1q-R in the ELISA. The selected hybridomas were grown in spinner flasks and the spent culture supernatant collected for antibody purification by protein A affinity chromatography. One of the monoclonal antibodies so produced against gC1q-R, 99-12-1, was tested to determine if it would compete with HIV-1 gp120 for binding to gC1q-R (see Example 11 below).

EXAMPLE 3

Making Polyclonal Antibodies Against gC1q-R

Two male New Zealand white rabbits, about fifteen weeks old, were immunized subcutaneously with 100 μg of purified E. coli expressed gC1q-R in complete Freund's adjuvant (Difco Laboratories). Two weeks later they were injected again with the same amount of the antigen in incomplete Freund's adjuvant. The same immunization was repeated two weeks later. Sera were collected from the immunized animals and tested for reactivity with gC1q-R in ELISA as described above except HRP conjugated donkey anti-rabbit IgG (Jackson ImmunoResearch Laboratories) at 1:2,000 dilution in BLOTTO was used for detection of the bound antibodies. The animal showing the higher serological response was used for collecting serum. Polyclonal rabbit anti-gC1q-R immunoglobulins were purified by an affinity column using gC1q-R coupled Affigel 102 (BioRad Laboratories).

EXAMPLE 4

Binding of HIV-1 IIIB gp120 to E. coli Expressed gC1q-R in ELISA

Wells of Immulon 2 plates were coated with 100 μl of E. coli expressed gC1q-R (5 μg/ml in 0.1M sodium acetate buffer at pH 6) and incubated overnight at room temperature. After the wells were treated with the blocking buffer PBSTB (PBST containing 2% bovine serum albumin) for 1 hour at room temperature and rinsed with PBST, 100 μl of serially diluted baculovirus expressed HIV-1IIIB gp120 (American Biotechnologies, Inc., Cambridge, Mass.) (from 2 μg/ml to 0.016 μg/ml) was added to the corresponding wells in duplicate for reaction for 1 hour at room temperature. The wells were then washed as before. The bound gp120 was detected by the anti-HIV-1 gp120 V3-domain murine monoclonal antibody BAT123 conjugated with HRP at a dilution of 1:2000. The antibody was tested to react with the peptidic segment in gp120 (amino acid residue nos. of HXB2R strain: 308–322) as shown in SEQ ID NO.: 7, and also not to interfere with the binding between gC1q-R and gp120. One hundred microliters of the diluted conjugate were added to each well for reaction for 1 hour at room temperature. The wells were then washed, and 200 μl of the peroxidase substrate solution was added to each well for color development for 30 minutes. The reaction was stopped by addition of 50 μl of 2M $H_2SO_4$, and OD measured by a BioTek ELISA reader at 450 nm. Specific reactivity is obtained by subtracting the OD of the rest well with gp120 added from that of the control weds without gp120.

Figure 2:
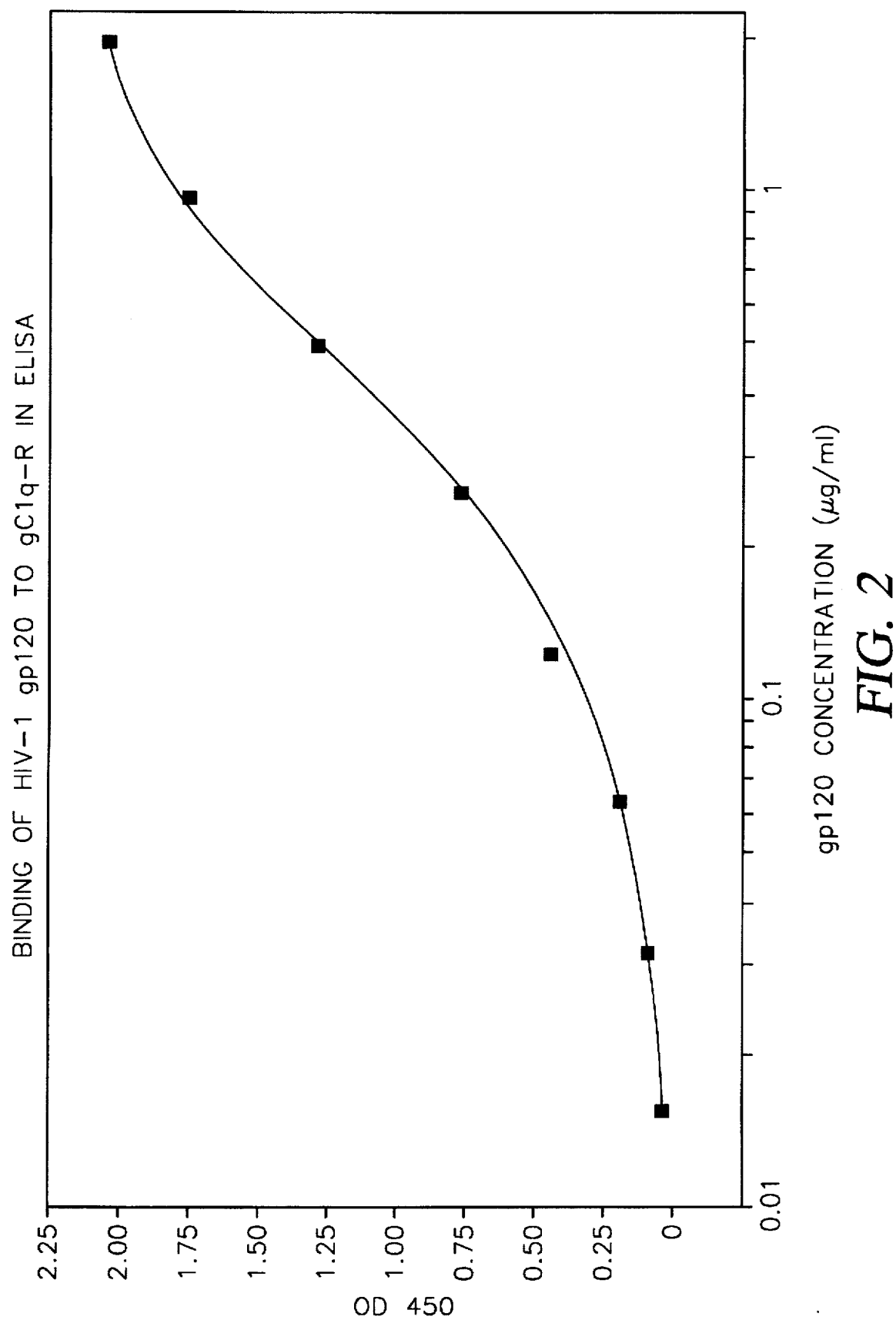
FIG. 2 shows the binding of HIV-1 gp120 to gC1q-R, as measured by ELISA. The Y axis represents the reactivity of HIV-1 gp120 with gC1q-R expressed as OD at 450 nm and the X axis is the concentration of HIV-1 gp120 in solution.

The results are shown in FIG. 2, where it can be seen that as gp120 concentration increases, the binding of gp120 to a constant amount of immobilized recombinant gC1q-R increases in a sigmoidal fashion. This shows a dose-dependent binding of g-p120 to gC1q-R. Inasmuch as the anti-gp120 V3 region antibody BAT123 is still able to react with gp120 bound to gC1q-R it shows that the binding of gC1q-R to gp120 does not involve the V3 region of gp120, as shown in SEQ ID NO.: 7.

EXAMPLE 5

HIV-1 Neutralization Assay

To test the inhibitory activity of gC1q-R on the infectivity of HIV-1, a syncytium-forming microassay using CEM-SS cells as targets was performed as described by P. L. Nara et al. (*AIDS Res. Hum. Retroviruses* 1987; 3:283–302). Briefly, 50 µl of diluted *E. coli* expressed gC1q-R was mixed with 50 µl viral culture supernatant containing 200 syncytium-forming units (SFUs) of HIV-1IIIB, HIV-1MN, or HIV-1RF, and incubated for 1 hour at room temperature. The mixtures were added into microculture wells containing $5\times10^4$ DEAE-dextran-treated CEM-SS cells, and the cell cultures were maintained in 5% $CO_2$ at 37° C. for three to four days. The syncytia were enumerated under an inverted microscope. The neutralizing activity was expressed as $IC_{50}$, defined as the concentration required to achieve 50% inhibition of the infection (i.e., Vn/Vo=50%), where Vn is the SFU in the test wells and Vo is the SFU in the control wells without test antibodies.

Figure 3A:
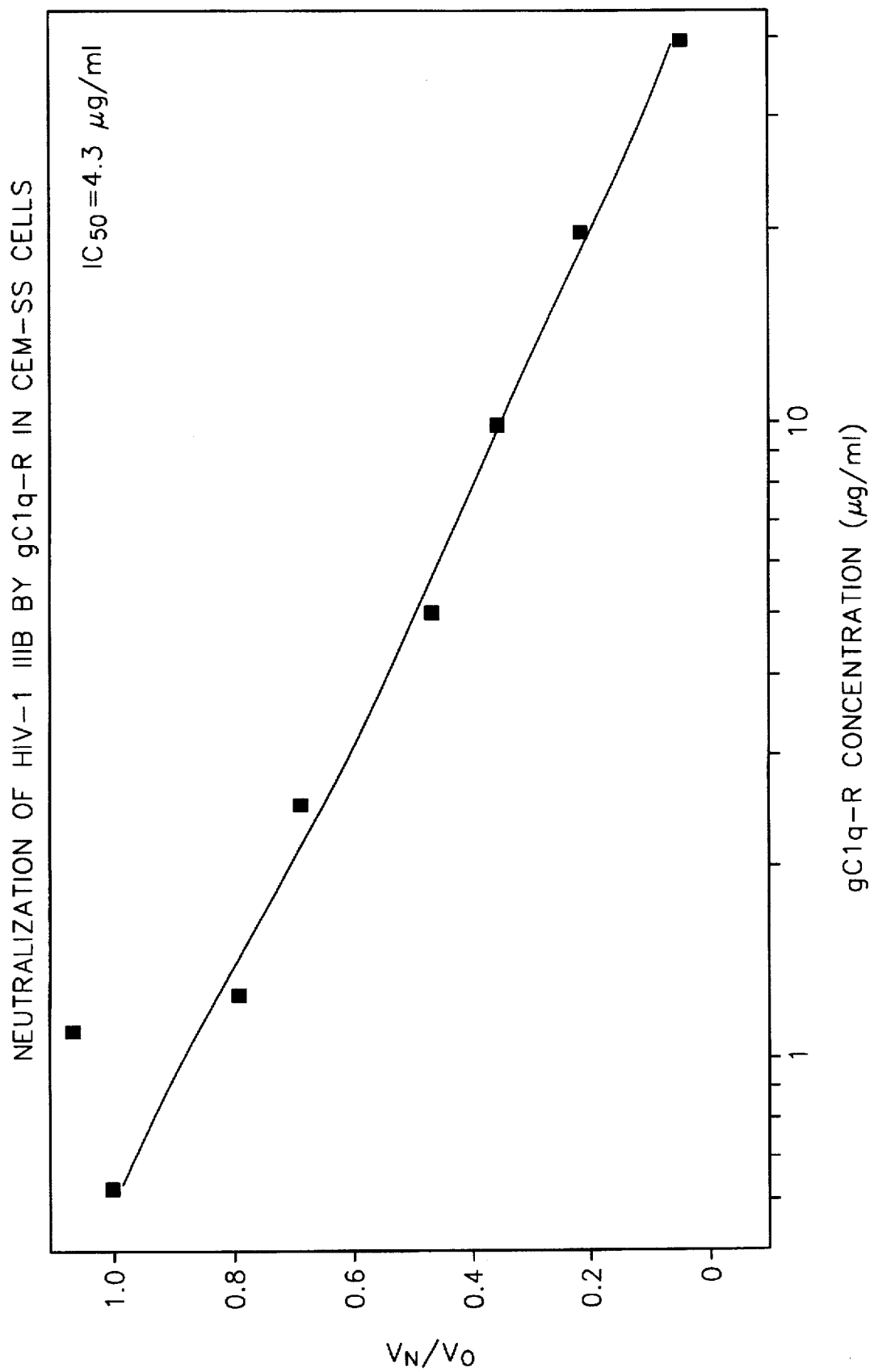
FIG. 3A shows the neutralization of the infectivity of HIV-1IIIB by gC1q-R in CEM-SS cells; where Vn is the mean number of syncytia in duplicate test wells, and Vo the mean number of syncytia in the duplicate control wells.
Figure 3B:
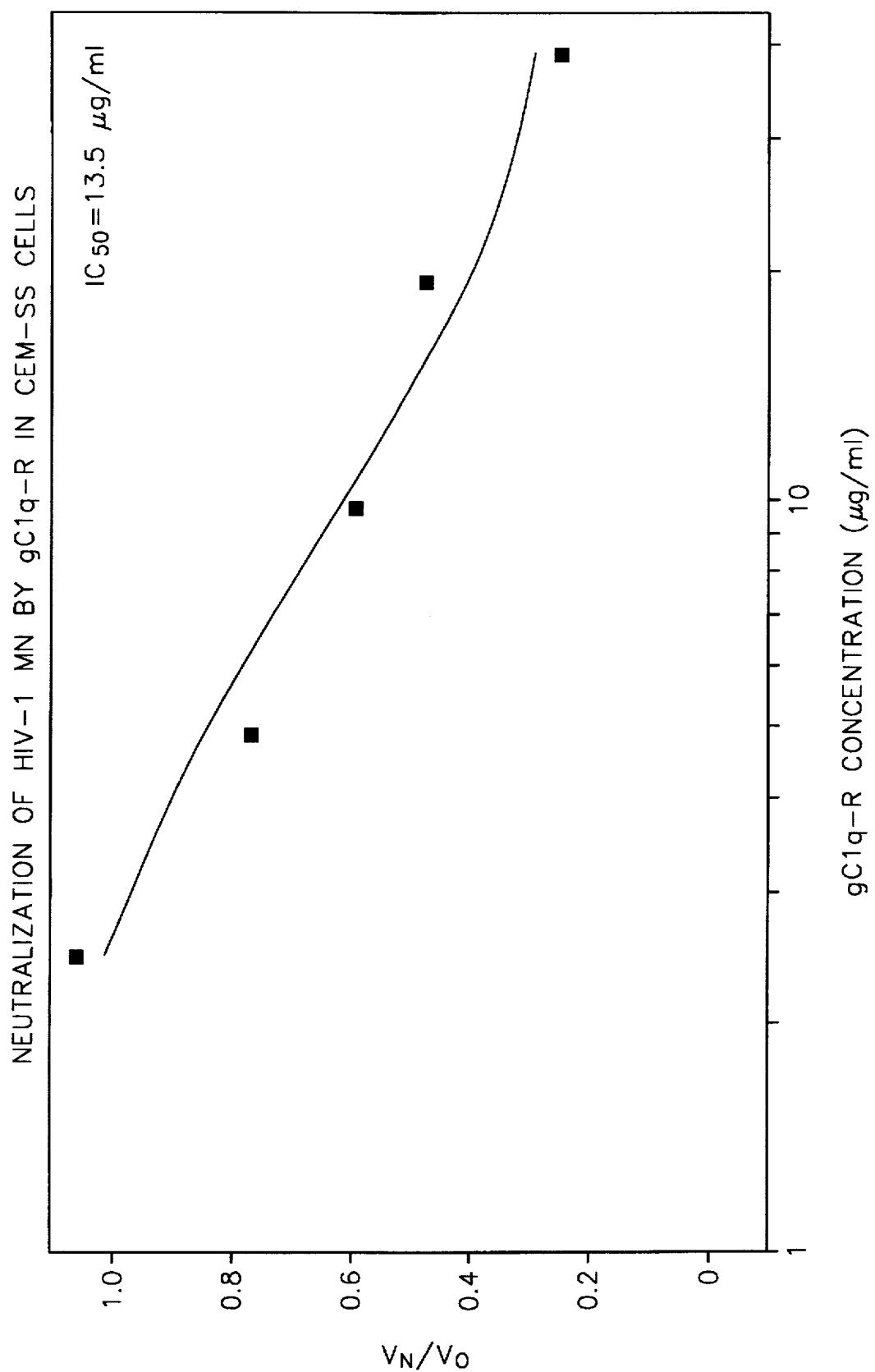
FIG. 3B shows the neutralization of the infectivity HIV-1MN by gC1q-R in CEM-SS cells; where Vn is the mean number of syncytia in duplicate test wells, and Vo the mean number of syncytia in the duplicate control wells.
Figure 3C:
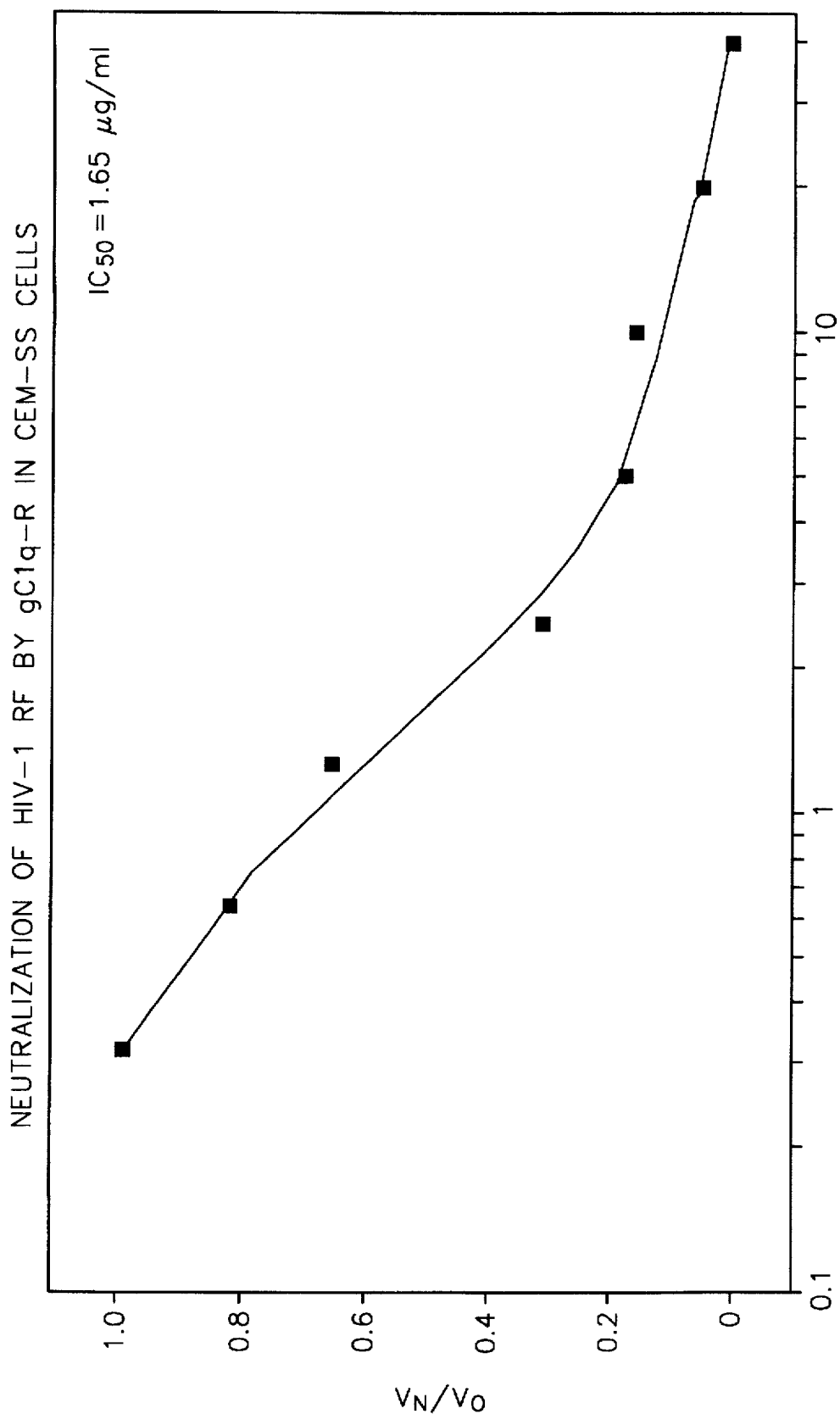
FIG. 3C shows the neutralization of the infectivity of HIV-1RF by gC1q-R in CEM-SS cells; where Vn is the mean number of syncytia in duplicate test wells, and Vo the mean number of syncytia in the duplicate control wells.

The results are shown in FIGS. 3A, 3B and 3C. It can be seen that gC1q-R neutralized HIV-1IIIB, MN, and RF with $IC_{50}$ of 4.3, 13.5, and 1.65 µg/ml, respectively. These neutralization data indicate that gC1q-R can broadly inhibit the infectivity of divergent HIV-1 isolates.

EXAMPLE 6

Assay for Inhibitory Activity on Syncytium Formation

The effects of gC1q-R on HIV-1 transmission via cell-to-cell fusion was studied using HIV-1-infected H9 cells and CD4-expressing HeLa cells (HeLa-CD4$^+$), which fuse upon contact and form syncytia in culture. HeLa is a human carcinoma cell line and HeLa-CD4$^+$ contains in its genome CD4 DNA introduced by transfection, and it expresses CD4 antigen on its cell surface. The procedure used in the present studies is similar to that described (P. J. Madden et al., *Cell* 1986; 47:333–348). In essence, HeLa-CD4$^+$ cells were plated onto wells of 24-well microculture plates at $1\times10^5$ cells per well. The plates were incubated for 36 hours and by this time, the monolayer epithelial cells were almost confluent. When $1\times10^4$ infected H9 cells were added to the sub-confluent HeLa-CD4$^+$ cells, the cells formed contacts and fused, and by 8 hours multinucleated giant cells (syncytia) formed. Those syncytia with more than five nuclei could be easily identified and enumerated, providing quantitative measurement of syncytium formation. When the effects of purified *E. coli*-expressed gC1q-R on syncytium formation were studied, gC1q-R at different concentrations as mixed with infected H9 cells and added to the HeLa-CD4$^+$ cells. The final total volume of the culture medium per well was 1 ml. At the end of the 8-hour incubation at 37° C. in 5% $CO_2$, the wells were washed with RPMI-1640 culture medium, fixed with methanol, air-dried, and stained with 0.1% methylene blue in methanol. The cells were examined at 100× magnification and the number of syncytia (of more than 5 nuclei) were determined in four randomly chosen fields and averaged. The percent inhibition of syncytium formation was calculated from the reduction in the number of syncytia in weds with gC1q-R added as compared to the control.

The results, shown in FIG. 4, demonstrate that recombinant gC1q-R inhibits the fusion between HIV-1IIIB-infected H9 cells and CD4$^+$-HeLa cells with $IC_{50}$ of 21 µg/ml.

EXAMPLE 7

Binding of gC1q-R to HIV-1IIIB-Infected H9 Cells as Measured by Flow Cytometry The binding of purified *E. coli* expressed gC1q-R to gp120 expressed on the surface of HIV-1IIIB-infected H9 cells was analyzed by indirect immunofluorescence flow cytometry. Fifty microliters of infected cells at $10\times10^6$ cells/ml in PBSB (phosphate-buffered saline with 1% bovine serum albumin at pH 7.4) was mixed with a serial concentration of purified *E. coli* expressed gC1q-R for 30 minutes on ice. The cells were then washed once in the same buffer by centrifugation at 300×g for 5 minutes. The cell pellet was then resuspended in 50 µl of the same buffer, and 50 µl of affinity purified rabbit anti-gC1q-R at 5 µg/ml was added for reaction on ice for 30 minutes. The cells were then washed as before, and 50 µl of fluorescein conjugated donkey anti-rabbit IgG (Jackson ImmunoResearch Laboratories) at 1:40 dilution was added, and incubated for another 30 minutes on ice. The cells were then washed, fixed in 1% paraformaldehyde and then analyzed using a Coulter EPIC cell analyzer (Coulter Electronics, Hialeah, Fla.). In the controls, only rabbit anti-gC1q-R and/or fluorescein conjugated donkey anti-rabbit IgG were used. Specific cell staining was calculated by subtracting the percent cell binding of the test from that of the control which was arbitrarily set at 10%. Uninfected H9 cells were also tested as negative control for the binding studies.

Figure 5:
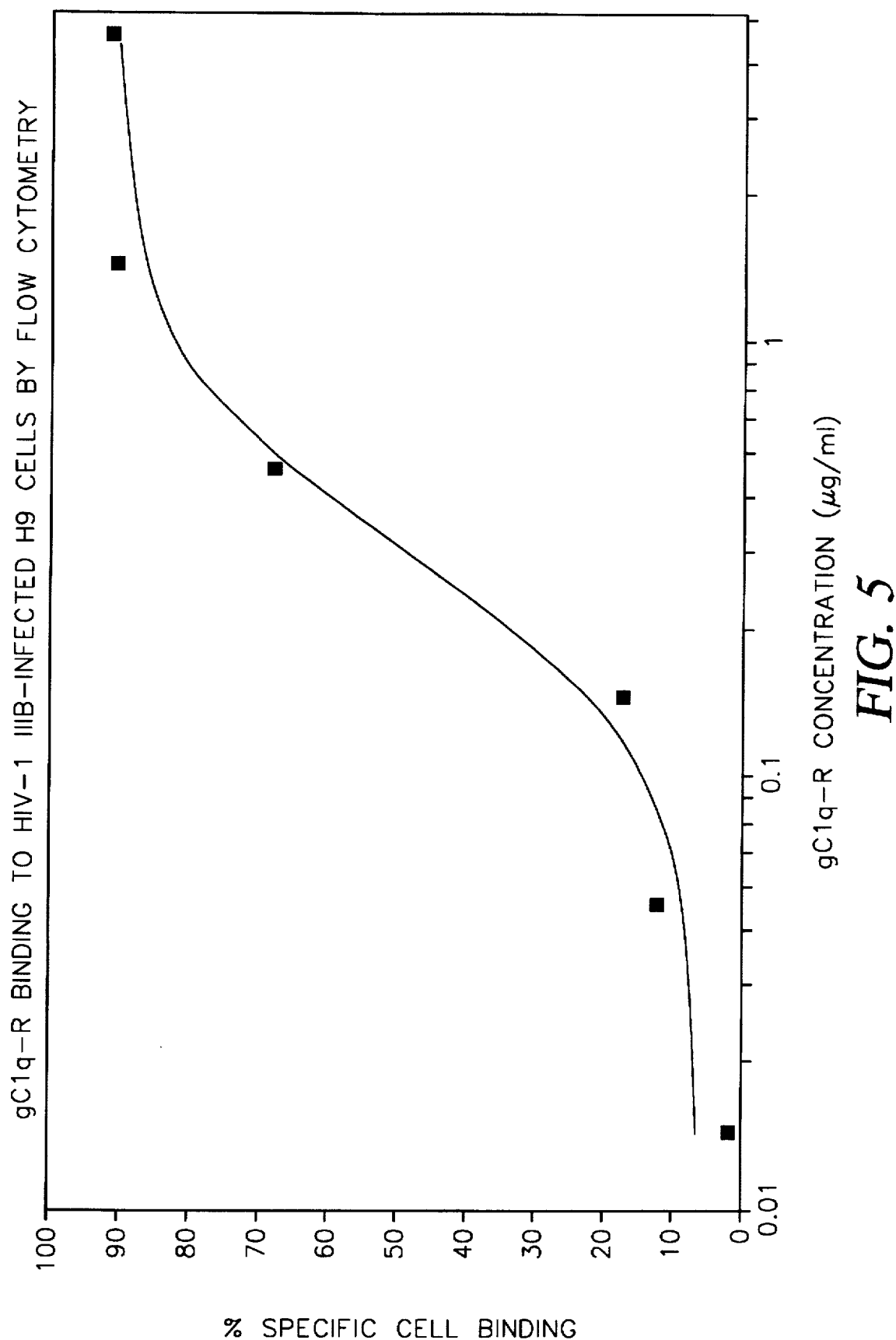
FIG. 5 shows the binding of purified *E. coli* expressed gC1q-R to HIV-1IIIB-infected H9 cells as determined by flow cytometry.

The results showed that recombinant gC1q-R bound to HIV-1IIIB-infected H9 cells in a dose-dependent manner (FIG. 5), but not to uninfected H9 cells.

EXAMPLE 8

Effect of C1q on HIV-1 gp120 Binding to gC1q-R in ELISA

To test whether the natural ligand C1q shares the same binding site for gC1q-R as gp120, the effect of C1q on the binding of HIV-1 gp120 to gC1q-R was studied by ELISA. Wells of Immulon 2 microtest plates were coated with 50 µl of 5 µg/ml purified *E. coli* expressed gC1q-R in 0.1M sodium acetate buffer and incubated overnight at room temperature. The wells were then blocked with 200 µl of a blocking/dilution buffer PBSTB for 1 hour at room temperature. After the wells were washed with PBST, 50 µl of baculovirus expressed HIV-1IIIB gp120 at 0.2 µg/ml were added to each well in the presence or absence of serially diluted *E. coli* expressed gC1q-R or purified C1q from human serum (Quidel, San Diego, Calif.) in the blocking/dilution buffer, and the wells were incubated for another hour at room temperature and then washed. Fifty microliters of HRP conjugated monoclonal antibody BAT123 at 1:2000 dilution in the blocking/dilution buffer was added to each well for 1 hour at room temperature. The plate was then washed, and peroxidase substrate solution added for color development as described above. Specific reactivity was obtained by subtracting the OD of test wells with gp120 added from that of control wells without gp120.

Figure 6:
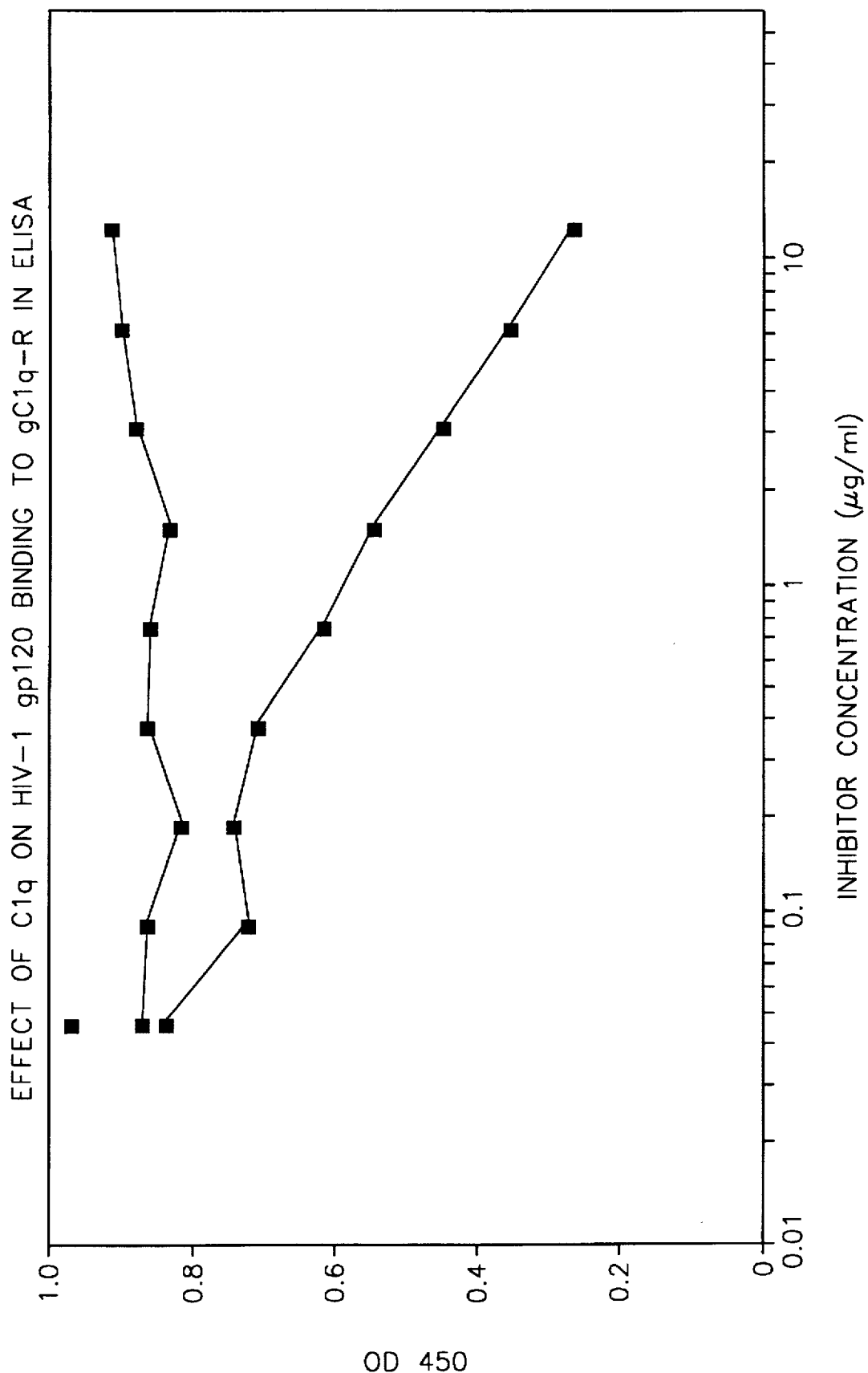
FIG. 6 shows the effect of C1q on HIV-1 gp120 binding to gC1q-R in ELISA. The line marked with filled circles represents C1q and the line marked with rifled squares represents gC1q-R. The Y axis represents the reactivity of gp120 with gC1q-R expressed as OD at 450 nm and the X axis is the concentration of C1q and gC1q-R in solution.

The results are shown in FIG. 6, where the line marked with filled circles represents C1q and the line marked with filled squares represents gC1q-R. C1q does not compete with the binding of gp120 to gC1q-R, whereas gC1q-R does as expected. This result indicates that gp120 binds to gC1q-R at a site distinct from that for C1q, and they are mutually non-interfering. This is a very important finding because when gC1q-R is administered into HIV-1-infected individuals or people exposed to HIV-1, the abundant amount of C1q present in the blood will not interfere with gC1q-R in binding to HIV-1 gp120 on the virions or infected cells. Furthermore, the ability of gC1q-R to bind both C1q and gp120 simultaneously is significant and beneficial, because gC1q-R may be able to mediate activation of the classical complement pathway to lyse HIV-1 virions and HIV-1-infected cells.

EXAMPLE 9

Reactivity of HIV-1 gp120 with Different Recombinant Constructs of gC1q-R

To locate the gC1q-R binding site for HIV-1 gp120, recombinant constructs of gC1q-R of varying lengths were made for ELISA. Wells of Immulon 2 microtest plates were coated with 100 µl of purified *E. coli* expressed full-length gC1q-R (1–209 a.a.), gC1q-R (58–209 a.a.), gC1q-R (1–94 a.a.), or gC1q-R (95–209 a.a.) at 5 µg/ml in 0.1M sodium acetate buffer (pH 6) and incubated overnight at room temperature. After the wells were treated with the blocking/dilution buffer PBSTB for 1 hour at room temperature and rinsed with PBST, 100 µl of serially diluted baculovirus expressed HIV-1IIIB gp120 (American Biotechnologies, Inc.) (from 2 µg/ml to 0.016 µg/ml) was added to the corresponding wells in duplicate for reaction for 1 hour at room temperature. The wells were then washed as before. The bound gp120 was detected by addition of 100 µl of HRP-conjugated monoclonal antibody BAT123 at dilution of 1:2000 for 1 hour at room temperature. The wells were then washed, and 200 µl of the peroxidase substrate solution was added to each well for color development for 30 minutes. The reaction was stopped by addition of 50 µl of 2M $H_2SO_4$, and the OD was measured by a BioTek ELISA reader at 450 nm. Specific reactivity was obtained by subtracting the OD of test wells with gp120 added from that of control wells without gp120.

Figure 7:
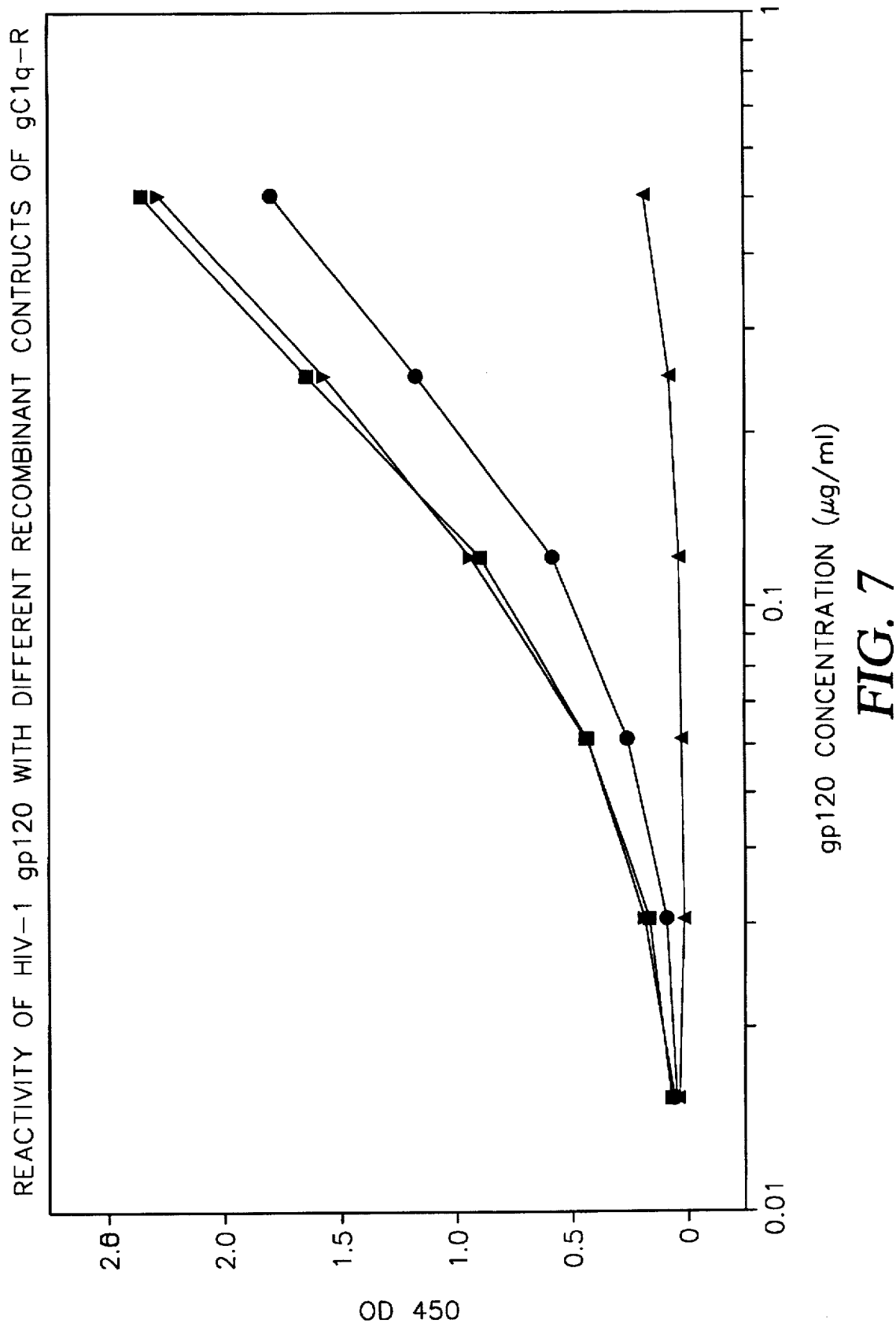
FIG. 7 shows the reactivity of HIV-1 gp120 with different forms of *E. coli* expressed gC1q-R as solid-phase antigen in ELISA. The line marked with filled squares represents the full-length mature form of gC1q-R (1–209 a.a.). The line marked with filled circles indicates the truncated gC1q-R (58–209 a.a. ), representing gC1q-R with deletion of the N-terminal 57 amino acids. The line marked with filled triangles represents the N-terminal construct, gC1q-R (1–94 a.a.). The line marked with filled inverted triangles represents the C-terminal construct, gC1q-R (95–209 a.a.). The Y axis represents the reactivity of HIV-1 gp120 with the different forms of gC1q-R expressed as OD at 450 nm and the X axis is the concentration of gp120 in solution.

The results are shown in FIG. 7, where the line marked with filled squares represents the full-length gC1q-R (1–209 a.a), the line marked with filled circles represents gC1q-R (58–209 a.a.), the line marked with filled triangles represents gC1q-R (1–94 a.a.), and the line marked with filled inverted triangles represents gC1q-R (95–209 a.a.). Gp120 binds to gC1q-R (1–209 a.a.), gC1q-R (58–209 a.a.) and gC1q-R (95–209 a.a.), but not to gC1q-R (1–94 a.a.). The results thus suggest that the binding site on gC1q-R to gp120 resides in its C-terminal portion. This observation is consistent with the result as shown in FIG. 6 that the gp120 binding site is distinct from that for C1q, which was mapped to the peptidic segment in the N-terminus of gC1q-R as shown in SEQ ID NO.: 8 (B. Ghebrehiwet et al., *J. Exp. Med.* 1994; 179:1809–1821). This peptidic segment is equivalent to the amino acid residue nos. 76–93 of SEQ ID NO.: 1.

EXAMPLE 10

Peptide Mapping of the Binding Domain for 99-12-1 on gC1q-R

To map the epitope for 99-12-1 binding on gC1q-R, the Multipin Peptide Synthesis techniques was used (H. M. Geysen et al., *Science* 1987; 235:1184–1190). Forty-one 12-mer peptides encompassing the entire sequence of gC1q-R (the consecutive peptides overlap each other by seven amino acids) were synthesized individually in a sequential manner on plastic pins in an array of a 96-well microtest plate. The peptide set was custom synthesized by Chiron Mimotopes PTY. LTD., Clayton, Victoria, Australia.

The procedure for epitope mapping using this multipin peptide system was similar to the manufacturer's instruction manual. Briefly, the pins were first treated with a pre-coat buffer containing 2% bovine serum albumin and 0.1% Tween 20 in PBS for 1 hour at room temperature. Then the pins were inserted into the individual wells of 96-well microtest plate containing antibody 99-12-1 in the pre-coat buffer at 2 µg/ml. The incubation was for 1 hour at room temperature. The pins were washed in PBST (3 rinses for every 10 minutes), and then incubated in the wells of a 96-well microtest plate containing 100 µl of HRP-conjugated goat anti-mouse IgG (Fc) (Jackson ImmunoResearch Laboratories) at a 1:4,000 dilution for 1 hour at room temperature. After the pins were washed as before, the pins were put into wells containing peroxidase substrate solution of diammonium 2,2'-azino-bis[3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate was read at 405 nm by a BioTek ELISA plate reader against a background absorption wavelength of 492 nm. Wells showing color development indicated reactivity of the gC1q-R derived peptides in such wells with 99-12-1.

The results of the epitope mapping show that 99-12-1 binds to the peptide of SEQ ID NO.: 2.

To confirm the binding epitope of 99-12-1, the peptide LM12DN of SEQ ID NO.: 2 was tested for binding to 99-12-1 in ELISA. The peptide of SEQ ID NO.: 8 (peptide TD18EE) which was defined, earlier as the binding site for C1q (B. Ghebrehiwet et al., *J. Exp. Med.* 1994; 179:1809–1821) was used as a negative control. Peptides LM12DN and TD18EE were synthesized by an automated peptide synthesizer (Applied Biosystems, Inc., Foster City, Calif.), using the 9-fluorenylmethoxycarbonyl synthesis protocol as described by the manufacturer's manual. In the peptide ELISA, wells of Immulon 2 microtest plates were coated with 50 µl of the peptides LM12DN or TD18EE at 1 µg/ml and incubated overnight at more temperature. After the coating solution was removed by flicking the plate, 200 µl of PBSTB were added to each well to saturate the non-specific sites for 1 hour at room temperature. The wells were then washed with PBST. Fifty microliters of serially diluted 99-12-1 in PBSTB were added in duplicate to the wells for 1 hour at more temperature. The plate was washed again. Fifty microliters of HRP-conjugated goat anti-mouse IgG (Fc) (Jackson ImmunoResearch Laboratories) at a dilution of 1:2,000 was added to each well for 1 hour at room temperature. After the wells were washed, peroxidase substrate was added for color reaction as described above. The plate was read at 450 nm by using an ELISA reader. Specific reactivity was obtained by subtracting the OD of test wells with 99-12-1 added from that of the control wells.

Figure 8:
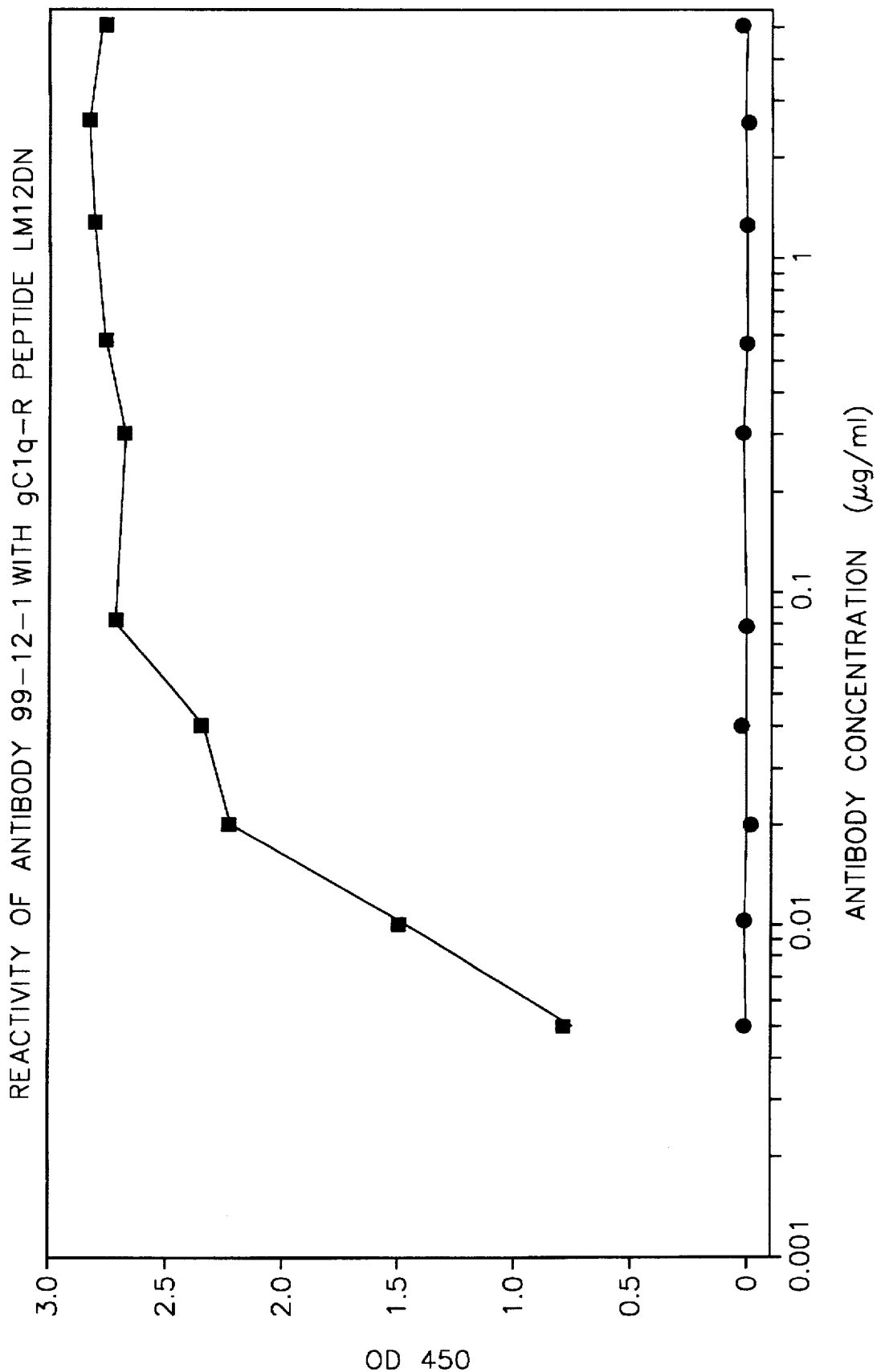
FIG. 8 shows the binding of antibody 99-12-1 to the gC1q-R peptide LM12DN. The line marked with filled squares represents the peptide LM12DN and the line marked with filled circles represents the peptide TD18EE. The Y axis represents the reactivity of 99-12-1 with the peptides expressed as OD at 450 nm and the X axis is the concentration of 99-12-1 in solution.

The results are shown in FIG. 8, where the line marked with filled squares represents the peptide LM12DN and the line marked with filled circles represents the peptide TD18EE. 99-12-1 binds to the peptide LM12DN (SEQ ID NO.: 2) in a dose-dependent manner, but not to the peptide TD18EE (SEQ ID NO.: 8).

EXAMPLE 11

Competition of the Binding of HIV-1 gp120 to gC1q-R by Anti-gC1q-R Monoclonal Antibody 99-12-1 in ELISA Wells of Immulon 2 microtest plates were coated with 50 µl of 5 µg/ml purified *E. coli* expressed gC1q-R in 0.1M sodium acetate buffer (pH 6) and incubated overnight at room temperature. The wells were then blocked with 200 µl of a blocking/dilution buffer PBSTB for 1 hour at room temperature, and then washed with PBST. Fifty microliters of baculovirus expressed HIV-1IIIB gp120 at 0.2 µg/ml were added to each well in the presence or absence of serially diluted 99-12-1 in the blocking/dilution buffer, and the wells were incubated for another hour at room temperature and then washed. Fifty microliters of HRP conjugated monoclonal antibody BAT123 at 1:2000 dilution in the blocking/dilution buffer was added to each well, followed by incubation for 1 hour at room temperature. The plate was then washed, and peroxidase substrate solution added for color development as before. The inhibition of the binding of gp120 to gC1q-R by 99-12-1 is calculated as the difference in OD between wells with or without 99-12-1.

Figure 9:
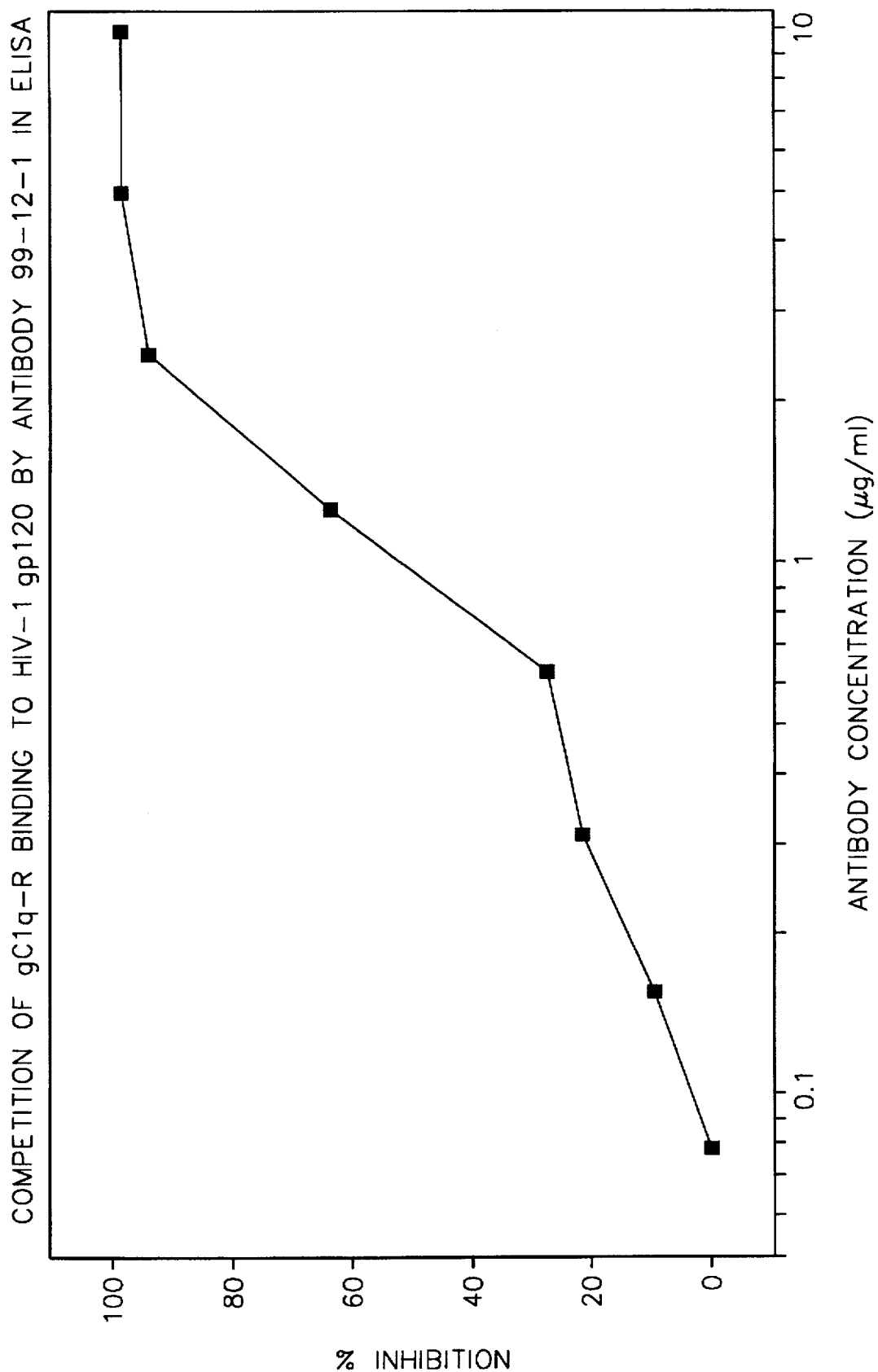
FIG. 9 shows the competition of gC1q-R binding to HIV-1 gp120 by anti-gC1q-R monoclonal antibody 99-12-1.

FIG. 9 shows that 99-12-1 inhibits the binding of gp120 to gC1q-R in a dose-dependent manner, suggesting that 99-12-1 binds to a site in gC1q-R crucial for the interaction with gp120. The site is mapped to SEQ ID NO.: 2 as described in Example 10.

EXAMPLE 12

Competition of gC1q-R Binding to HIV-1 gp120 by Antibodies G3-299 and 6205 in ELISA In order to help identify the gC1q-R binding site on HIV-1 gp120, a competition ELISA was designed to examine the effects of various anti-HIV-1 g-p120 antibodies and recombinant soluble CD4 (rsCD4) on the binding of gp120 to gC1q-R.

Wells of Immulon 2 microtest plates were coated with 50 µl of 5 µg/ml purified E. coli expressed gC1q-R in 0.1M sodium acetate buffer (pH 6) and incubated overnight at room temperature. The wells were then blocked with 200 µl of a blocking/dilution buffer PBSTB for 1 hour at room temperature. Fifty microliters of baculovirus expressed HIV-1IIIB gp120 at 0.2 µg/ml was added to each well in the presence or absence of serially diluted anti-HIV-1 gp120 antibodies or rsCD4 (Biogen, Boston, Mass.) in the blocking/dilution buffer, and the wells were incubated for another hour at room temperature. The anti-HIV-1 gp120 antibodies tested included: murine monoclonal antibody G3-299 (to the C4 region (amino acid residue nos. of HXB2R strain: 423–437), as shown in SEQ ID NO.: 9), sheep anti-HIV-1 gp120 C5 region antibody, 6205 (to the sequence of amino acid residue nos. of HXB2R strain: 497–511, as shown in SEQ ID NO.: 10), and BAT085 (to the V2 region of amino acid residue nos. of HXB2R strain: 169–183, as shown in SEQ ID NO.: 11). The properties of G3-299 and BAT085 were described previously (N. C. Sun et al., *J. Virol.* 1989; 63:3579–3585; M. S. C. Fung et al., *J. Virol.* 1992; 66:848–856). Antibody 6205 was purchased from International Enzymes, Fallbrook, Calif. After the plate was washed, 50 µl of HRP conjugated monoclonal antibody BAT123 at 1:2,000 dilution in the blocking/dilution buffer were added to each well, followed by incubation for 1 hour at more temperature. The plate was then washed, and peroxidase substrate solution added for color development as before. The percent inhibition of the binding of gp120 to gC1q-R by anti-HIV-1 g-p120 antibodies or rsCD4 is calculated as the difference in OD between wells with or without the competing agents.

Figure 10:
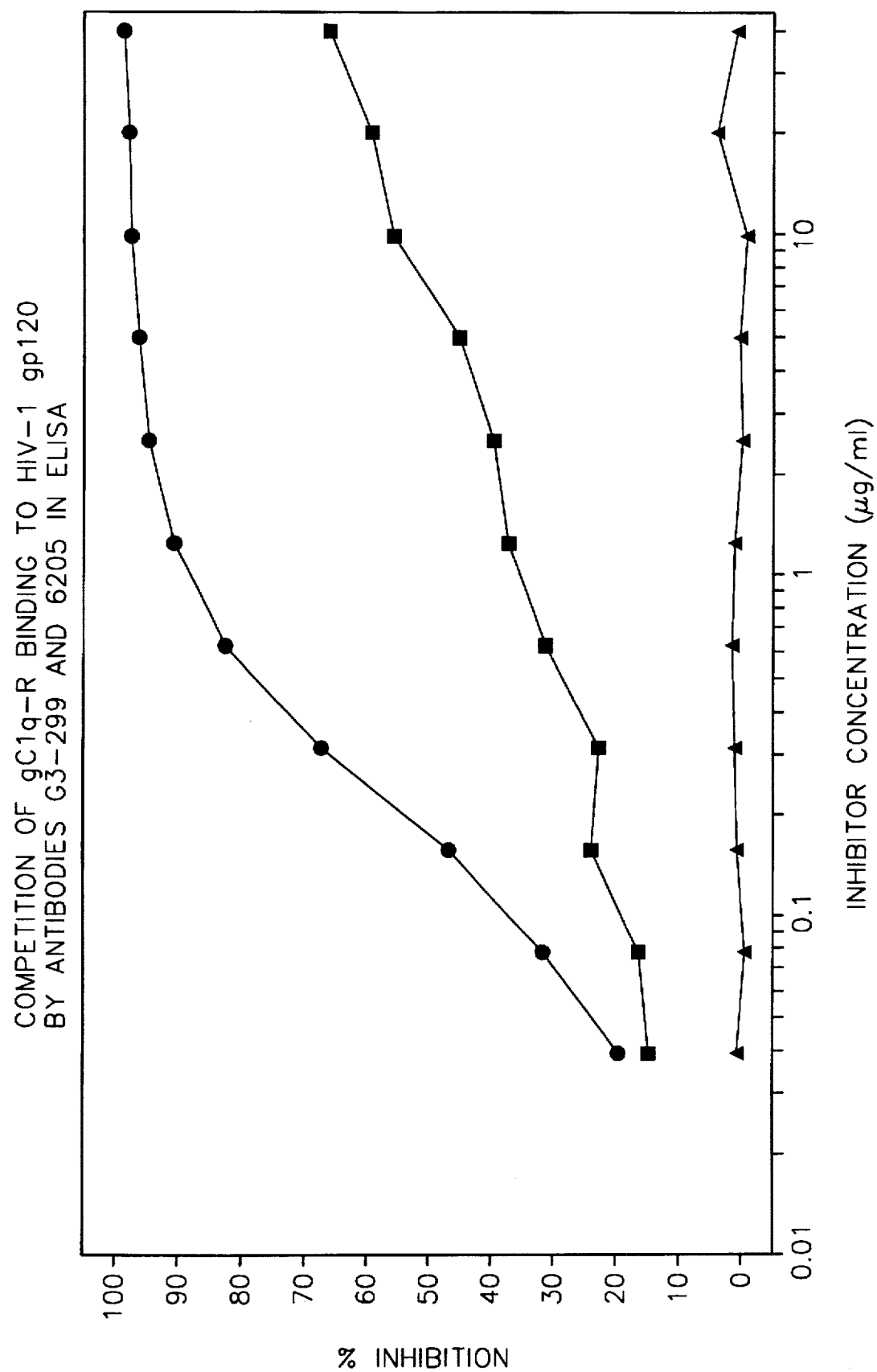
FIG. 10 shows the competition of HIV-1 gp120 binding to gC1q-R by anti-HIV-1 gp120 antibodies G3-299 and 6205. The line marked with filled circles represents anti-HIV-1 gp120 C4 region G3-299, the line marked with filled squares represents polyclonal sheep antibody 6205, which is specific against the HIV-1 gp120 C5 region peptide (amino acid residue numbers of HXB2R: 497–511, SEQ ID NO.: 10), and the line marked with solid triangles represents recombinant soluble CD4 (rsCD4).

The results are shown in FIG. 10, where the line marked with solid circles represents anti-gp120 C4 region G3-299, the line marked with solid squares represents polyclonal sheep anti-gp120 C5 region, 6205, the line marked with solid triangles represents rsCD4. It can be seen that G3-299 competes very effectively the gp120 binding to gC1q-R, and moderately for 6205; whereas rsCD4 does not. The antibody BAT085 to the V2 region also does not inhibit the binding. Taken together, the results from Examples 4 and 12 indicate that the gC1q-R Binding Site resides in the proximity of the C4 and C5 regions. It is distinct from the CD4 binding site. This important finding suggests that both gC1q-R and rsCD4 can be applied in combination for treatment of HIV-1 infection. This may broaden the effectiveness of preventing the infection of both CD4-positive and CD4-negative target cells.

EXAMPLE 13

Peptide Mapping of the Binding Domain for gC1q-R on HIV-1 gp120

To determine the peptide epitope of gC1q-R binding domain on HIV-1 gp120, the Multipin Peptide Synthesis techniques were again used as described above. Ninety-four 12-mer peptides encompassing the entire sequence of HIV-1MN gp120 (the consecutive peptides overlap each other by seven amino acids) were synthesized on plastic pins in an array for a 96-well microtest plate by Chiron Mimotopes Peptide Systems. The amino acid sequence of HIV-1MN gp120 was based on the Los Alamos National Laboratory's database (G. Myers et al., *Human Retroviruses and AIDS*, 1992). The procedure for epitope mapping is similar to that set forth in Example 10 above.

Purified E. coli expressed gC1q-R at 5 µg/ml was used to react with the peptides on the plastic pins. After the pins were washed the bound gC1q-R was detected by reaction with affinity purified rabbit anti-gC1q-R immunoglobulin for 1 hour at more temperature. The pins were rinsed as before, and reacted with donkey anti-rabbit IgG conjugated with HRP (Jackson ImmunoResearch Laboratories). The procedure for color development was the same as before.

Confirmation of the binding epitope of gC1q-R on HIV-1 gp120 was carried out by using overlapping synthetic peptides covering the binding region as coating antigen in ELISA. HIV-1 HXB2R gp120 overlapping peptides RC16GG (amino acid residue nos.: 444–459, as shown in SEQ ID NO.: 3), RC12LT (amino acid residue nos.: 444–455, as shown SEQ ID NO.: 12), and TG12NN (amino acid residue nos.: 450–461, as shown SEQ ID NO.: 13) were purchased from American Biotechnologies, Inc. Wells of Immulon 2 microtest plates were coated with 100 µl of the corresponding peptides at 2 µg/ml for overnight at room temperature. The wells were then treated with 200 µl of a blocking/dilution buffer PBSTB for 1 hour at room temperature. The wells were then washed with PBST. Purified E. coli expressed gC1q-R at different concentrations was added in duplicate to the wells for reaction for 1 hour at room temperature. The plates were then washed as before. One hundred microliters of affinity purified rabbit anti-gC1q-R immunoglobulin at 2 µg/ml were added to each well for 1 hour at room temperature. The plate was then washed. One hundred microliters of diluted HRP conjugated donkey anti-rabbit IgG were added for another hour at room temperature, and the plate was washed. Peroxidase substrate solution was added as before for color development.

The results are shown in FIG. 11, where the line marked with filled squares represents RC12LT, the line marked with filled circles represents TG12NN, and the line marked with filled triangles represents RC16GG. It can be seen that only RC16GG reacted with gC1q-R. This result is consistent with the face that the gC1q-R binding site on gp120 is located in the peptidic segment as shown in SEQ ID NO.: 3, which is located in the C4 region of gp120. The antibody G3-299 can compete effectively the binding of gp120 to gC1q-R as shown in Example 12, probably because of the close proximity between the binding site of G3-299 (SEQ ID NO.: 9) and that of gC1q-R (SEQ ID NO.: 3).

It should be understood that the terms, expressions and examples set forth herein are exemplary only and not limiting, and that the scope of the invention is defined only by the claims which follow, and includes all equivalents of such claimed subject matter.

What is claimed is:

1. The monoclonal antibody 99-12-1 produced by hybridoma, ATCC HB 11863.

2. The hybridoma cell line, ATCC HB 11863, producing the monoclonal antibody 99-12-1.

* * * * *